(12) United States Patent
Aerts

(10) Patent No.: US 7,528,153 B2
(45) Date of Patent: May 5, 2009

(54) DEOXYNOJIRIMYCIN ANALOGUES AND THEIR USES AS GLUCOSYLCERAMIDASE INHIBITORS

(75) Inventor: Johannes Maria Franciscus Gerardus Aerts, Abcoude (NL)

(73) Assignee: Genzyme Corporation, Cambridge, MA (US)

( * ) Notice: Subject to any disclaimer, the term of this patent is extended or adjusted under 35 U.S.C. 154(b) by 37 days.

(21) Appl. No.: 10/595,589

(22) PCT Filed: Oct. 29, 2004

(86) PCT No.: PCT/NL2004/000761

§ 371 (c)(1),
(2), (4) Date: Apr. 28, 2006

(87) PCT Pub. No.: WO2005/040118

PCT Pub. Date: May 6, 2005

(65) Prior Publication Data

US 2007/0066581 A1 Mar. 22, 2007

(30) Foreign Application Priority Data

Oct. 29, 2003 (EP) .................................. 03078395

(51) Int. Cl.
*A61K 31/445* (2006.01)
*C07D 401/00* (2006.01)
*C07D 211/06* (2006.01)

(52) U.S. Cl. ....................... 514/317; 514/319; 546/192; 546/195

(58) Field of Classification Search ....................... None
See application file for complete search history.

(56) References Cited

U.S. PATENT DOCUMENTS

| 4,855,415 | A | 8/1989 | Sugiyama et al. |
| 6,177,447 | B1 | 1/2001 | Aerts |
| 6,235,737 | B1 | 5/2001 | Styczynski et al. |
| 2004/0204379 | A1 | 10/2004 | Cheng et al. |
| 2006/0074107 | A1 | 4/2006 | Butters et al. |
| 2006/0264467 | A1 | 11/2006 | Mugrage et al. |
| 2007/0015793 | A1 | 1/2007 | Hirth et al. |
| 2007/0066581 | A1 | 3/2007 | Aerts |
| 2007/0135487 | A1 | 6/2007 | Aerts |

FOREIGN PATENT DOCUMENTS

| BR | 9902585 A | 9/2000 |
| WO | WO 98/02161 A | 1/1998 |
| WO | WO 02/055498 A | 7/2002 |
| WO | WO 2004/007453 A | 1/2004 |
| WO | WO 2004/007454 A | 1/2004 |
| WO | WO2004054975 A1 | 1/2004 |
| WO | WO2005039578 A2 | 6/2005 |

OTHER PUBLICATIONS

Overkleeft H S et al: "Generation of Specific Deoxynojirimycin-type Inhibitors of the Non-lysosomal Glucosylceramidase," Journal of Biological Chemistry, American Society for Biochemistry and Molecular Biology, Inc., vol. 273, No. 41, Oct. 9, 1998, pp. 26522-26527.
Science IP, The CAS Search Service, Freedom to Operate Search, Sep. 26, 2008, 96 pp.
Dwek, R.A., Targeting Glycosylation as a Therapeutic Approach Nature Reviews Drug Discovery, vol. 1, No. 1, 2002, pp. 65-75.
Omar, M., The clinical efficacy of a second-generation alpha-glucosidase inhibitor in non-insulin-dependent diabetic patients, South African Medical Journal, vol. 71, No. 7, 1987, pp. 422-423.
Federlin, K., The effect of two new glucosidase inhibitors on blood glucose in healthy volunteers and in type III diabetics, ACTA Diabetologica Latina, vol. 24, No. 3, 1987, pp. 213-221.

*Primary Examiner*—Raymond J Henley, III

(57) ABSTRACT

The invention provides a new class of deoxynojirimycin analogues, or pharmaceutically acceptable salts thereof which can suitably be used for the treatment of a disease selected from the group consisting of insulin resistance, Gauger disease, inflammatory diseases, hyperpigmentation and/or inflammatory skin conditions, overweight and obesity, lysosomal storage disorders, fungal diseases, melanoma and other tumors, and microbacterial infections. The invention further provides a pharmaceutical composition comprising said deoxynojirimycon analogue, or pharmaceutically acceptable salt thereof, and a pharmaceutically acceptable carrier.

Figure 1:
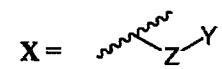
Figure 1:
Figure 1:
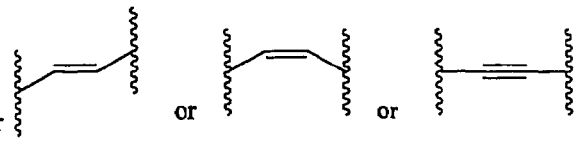
Figure 1:
Figure 1:
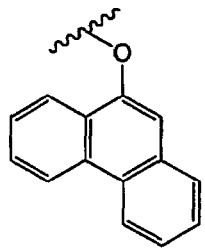
Figure 1:
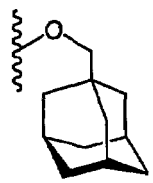
Figure 1:
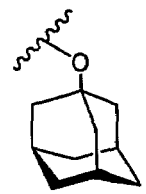
Figure 1:
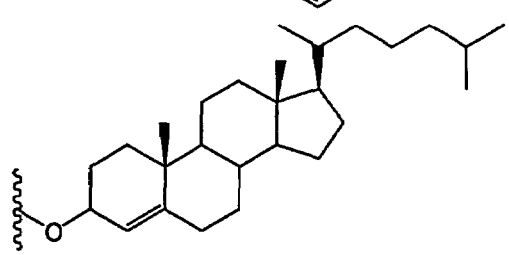
Figure 1:
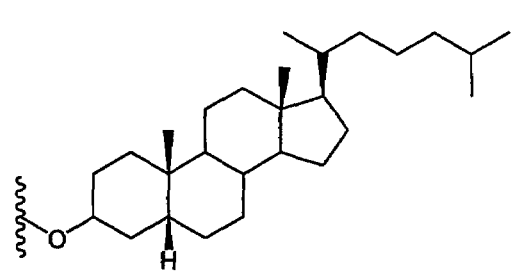

18 Claims, 4 Drawing Sheets o = 0 - 9
p = 0 - 9
q = 0 - 9

DEOXYNOJIRIMYCIN ANALOGUES AND THEIR USES AS GLUCOSYLCERAMIDASE INHIBITORS

FIELD OF THE INVENTION

The present invention relates to deoxynojirimycyin analogues, or pharmaceutically acceptable salts thereof, that can suitably be used for the treatment of various diseases in which the synthesis of glucosylceramide and/or other glucosphingolipids play a role. Such diseases include insulin resistance (diabetes mellitus type II), obesity and overweight, glucosphingolipid storage disorders, inflammation, hyperpigmentation and skin inflammatory conditions, melanoma and other tumors, fungal infections, viral infections, microbial infections and endotoxins.

Glycosphingolipids

Glycosphingolipids are denominated as those lipid molecules that comprise a ceramide moiety linked to a chain of sugars. The ceramide moiety is composed of one characteristic long chain amino alcohol, mostly D-erythro-C16-sphingosine, coupled via an amide bond to a fatty acid that may vary in length and degree of saturation. Several hundreds of specific glycosphingolipids exist due to variability in their oligosaccharide moiety that differs in number and nature of sugar units and their glycosidic bonds. Glycosphingolipids are classified into series such as for example gangliosides and globosides (see ref. 1).

For several decades glycosphingolipids have been considered as rather exotic structures and received little attention in mainstream biochemistry. Their complex composition and low abundance have limited research efforts to few pioneering expert groups. Their physiological relevance has largely remained mysterious since no clear function could be attributed to specific glycosphingolipids, with exception of those that act as blood group antigen.

In the human body glycosphingolipids and their sphingolipid precursor ceramide occur inside and outside cells. In the epidermis, ceramide and glucosylceramide molecules are abundantly present as free entities as well as protein-bound structures and they contribute to the water permeability and integrity of the skin (see ref. 2). Exchange of glycosphingolipids between the liver, a prominent site of their synthesis, and peripheral tissues is mediated by lipoproteins which contain significant amount of these lipids. In cells, glycosphingolipids are more or less exclusively located in the outer leaflet of the plasma membrane, their oligosaccharide chains being exposed to the environment. The ceramide lipid backbone provides sphingolipids with special physical properties (see ref. 3). In the presence of cholesterol they can segregate from the bulk of the membrane phospholipids, aggregating into a more ordered, but still fluid 'liquid-ordered', domain. Membrane proteins involved in signalling concentrate in these glycosphingolipid-cholesterol enriched microdomains (or 'rafts') (see ref. 4).

The composition of glycosphingolipids at the cell surface may vary with cell growth, differentiation, viral transformation, ontogenesis and oncogenesis (see ref. 5). It has become clear that gangliosides are particularly abundant in neuronal cells. As structural components they are essential for the function of the nervous system. Glycosphingolipids are as components of microdomains involved in the transduction of a multitude of extracellular signals into the interior of the cells (see ref. 6). Moreover, sphingolipids such as ceramide and its metabolites sphingosine(-1-phosphate) are thought to play a direct role as signalling molecules in a variety of cellular processes (see ref. 7, 8 and 9).

Glycosphingolipid Synthesis and Degradation

The synthesis and degradation of glycosphingolipids is a complex, multi-step process taking place in various intracellular compartments (see ref. 10 and 11). The enzymes involved in ceramide biosynthesis are localized on the cytosolic leaflet of the endoplasmic reticulum. The biosynthesis starts with the condensation of the amino acid serine with a palmitoyl coenzyme A by serine palmitoyl transferase to yield 3-ketosphinganine. Next, this is reduced to D-erythro-sphinganine by 3-ketosphinganine reductase and subsequently acylated to dihydroceramide by a N-acyltransferase. Dihydroceramide is largely desaturated to ceramide by the action of dihydroceramide desaturase.

Further metabolism of ceramide to three distinct categories of sphingolipids occurs: sphingomyelin, galactosylceramide and derivatives or glucosylceramide and derivatives. Ceramide is converted to sphingomyelin by the transfer of phosphorylcholine from the phospholipid phosphatidylcholine on the 1-hydroxyl group of ceramide. Diacylglycerol is liberated in this reaction. Sphingomyelin biosynthesis occurs on the luminal part of Golgi membranes but also other sites have been considered. The synthesis of galactosylceramide occurs in the lumen of the endoplasmatic reticulum and is catalyzed by a specific β-galactosyltransferase of which UDP-galactose is the co-substrate. Galactosylceramide, and its sulphated derivative sulphatide, are only synthesized in specific cell types. They play for example a crucial role in the formation and stability of myelin in the central nervous system. Glucosylceramide is formed by glucosylceramide synthase that is located on the cytosolic leaflet of the Golgi apparatus. The enzyme uses UDP-glucose as co-substrate and catalyzes the β-glycosidic linkage of glucose to the 1-position of ceramide. Glucosylceramide subsequently translocates through the Golgi membrane to reach the inner leaflet. From here, it can reach the plasma membrane or can be modified by further glycosylation in the Golgi apparatus. Lactosylceramide, the common precursor of glycosphingolipids in vertebrates, is formed by the addition of a galactose moiety from UDP-Gal catalysed by galactosyltransferase I. Next a variety of glycosphingolipids can be formed by stepwise glycosylation that is performed by only a few glycosyltransferases of limited specificity. Like on an assembly line, they transfer carbohydrate- and sialic acid residues to glycosyl acceptors. A prominent series of glycosphingolipids is the ganglio-series. Biosynthesis of complex gangliosides requires the activity of sialyltransferases I, II and III, GalNac transferase, galactosyltransferase II and sialyltransferases IV and V.

Degradation of glycosphingolipids occurs in specialised acidic compartments of cells, the lysosomes. Lysosomal glycosidases, assisted by activator proteins, sequentially cleave off the sugar residues from the non-reducing end of their glycolipid substrates and the remaining ceramide is finally hydrolysed by lysosomal ceramidase to yield free fatty acid and sphingosine. The released monosaccharides, sialic acids, fatty acids and sphingoid bases can leave the lysosome and may be used again for biosynthetic purposes. More recently it has been realized that degradation of glycosphingolipids may also occur outside lysosomes. For example a non-lysosomal glucosylceramidase has been discovered that is able to hydrolyse glucosylceramide to ceramide (see ref. 12). The latter enzyme is clearly distinct from the lysosomal glucosylceramidase (glucocerebrosidase) that is deficient in Gaucher disease patients. The physiological importance of extra-lysosomal degradation is still poorly understood, although it seems likely that the associated formation of ceramide may act as a signal and regulate cell behaviour (see ref. 13).

Glycospingolipid Storage Disorders

Glycosphingolipids are continuously synthesized and degraded in cells. A number of inherited diseases in man are characterized by intralysosomal glycosphingolipid accumulation. These so called glycosphingolipid storage disorders are caused by defects in lysosomal degradation (see ref. 13). Examples are GM1 gangliosidosis, Sandhoff disease (GM2 gangliosidosis, type II or variant O), Tay-Sachs disease (GM2 gangliosidosis, type I or variant B), Fabry disease (a-galactosyl-lactosylceramidosis), lactosylceramidosis, Gaucher disease (glucocerebrosidosis). Other sphingolipidoses are multiple sulphatase deficiency syndrome (mucosulphatidosis), Krabbe disease (global cell leukodystrophy, galactocerebrosidosis), Niemann-Pick disease (sphingomyelinosis, Farber disease (ceramidosis).

Gaucher Disease

Gaucher disease is the most frequently encountered lysosomal storage disorder in man (see ref. 14 and 15). In 1882 the clinical features of the disease were firstly described in detail by the French medical student Philippe C. E. Gaucher, reporting the presence of large unusual cells in a 32-year old female with an enlarged spleen. Already at the beginning of the last century it was suggested that the disease was a familial disorder. In 1934 the primary storage material in Gaucher disease was finally identified as glucocerebroside (glucosylceramide). The glycosphingolipid glucocerebroside is the common intermediate in the synthesis and degradation of gangliosides and globosides. It has been shown that the primary defect in Gaucher disease is a marked deficiency in activity of the lysosomal enzyme glucocerebrosidase (EC. 3.2.1.45) (see ref. 16 and 17). Inherited deficiencies in glucocerebrosidase result in accumulation of its lipid substrate in the lysosomal compartment of macrophages throughout the body. Three different phenotypes are recognized, which are differentiated on the basis of the presence or absence of neurological symptoms. More recently additional phenotypes of Gaucher disease have been identified. For example, complete deficiency in glucocerebrosidase activity results in major skin permeability abnormalities with lethal consequences either prenatally or shortly after birth. The most prevalent variant of the disease is the non-neuronopathic form, named type 1 Gaucher disease. The age of onset and clinical manifestations of type 1 Gaucher disease are highly variable. The most common symptoms include splenomegaly with anaemia and thrombocytopenia, mostly due to hypersplenism, hepatomegaly and bone disease. Anaemia may contribute to chronic fatigue. Thrombocytopenia and prolonged clotting times may lead to an increase in bleeding tendency. Atypical bone pain, pathological fractures, avascular necrosis and extremely painful bone crises may also have a great impact on the quality of life. Type 1 Gaucher disease is relatively common in all ethnic groups. It is prevalent among Ashkenazim with a carrier frequency as high as about 1 in 10 and an incidence of about 1 in 5000. The most common mutation in the glucocerebrosidase gene of Caucasians, including Ashkenazim, encodes the amino acid substitution N370S. The heteroallelic presence of the N370S mutation is always associated with a non-neuronopathic course. It has been demonstrated that the N370S glucocerebrosidase is normally produced and present in lysosomes. Its catalytic activity is only severely impaired at pH values above 5.0, illustrating the subtle nature of the mutation (see ref. 18). Most, but not all homozygotes for the N370S mutation do not develop significant clinical symptoms. Twin studies and the poor predictive power of phenotype-genotype investigations in Gaucher disease have clearly pointed out that epigenetic factors also play a key role in Gaucher disease manifestation (see ref. 19 and 20). Although glucocerebrosidase is present in lysosomes of all cell types, type 1 Gaucher disease patients solely develop storage of glucocerebroside in cells of the mononuclear phagocyte system. Macrophages participate in the degradation of invading microbes, the natural turnover of blood cells and in tissue modelling. In view of this it is not surprising that in a considerable number of the lysosomal storage disorders accumulation of storage material also takes prominently place in tissue macrophages. The type 1 variant of Gaucher disease is unique with respect to the fact that lysosomal storage occurs exclusively in macrophages. It is believed that the storage material stems from the breakdown of exogenous lipids derived from the turnover of blood cells. The glucocerebroside-loaded cells show a characteristic morphology with a 'wrinkled paper'-like appearance of their cytoplasm which contains lysosomal inclusion bodies; these cells are referred to as Gaucher cells. In the last decades it has become apparent that Gaucher cells are not inert containers of storage material but viable, chronically activated macrophages that contribute to the diverse clinical manifestations of Gaucher disease. Increased circulating levels of several pro-inflammatory cytokines (TNF-alfa, IL-1 beta, IL-6 and IL-8), the anti-inflammatory cytokine IL-10, and M-CSF have been reported (see ref. 21 and 22). It has been hypothesized that cytokine abnormalities may play a crucial role in the development of common clinical abnormalities in Gaucher patients such as osteopenia, activation of coagulation, hypermetabolism, gammopathies and multiple myeloma and hypolipoproteinaemias. More recently, examination of gene expression profiles by suppressive subtraction hybridisation analysis of Gaucher and control spleens has led to the identification of over-expression by Gaucher cells of transcripts for cathepsins B, K and S (see ref. 23). It is of interest to note that osteoclast derived cathepsin K is prominently involved in osseous type I collagen destruction. Local release of this cathepsin may contribute to the osteolysis in Gaucher disease.

Therapy of Gaucher Disease

Type 1 Gaucher disease has generally been considered to be the most attractive candidate among the inherited lysosomal storage disorders for developing effective therapeutic interventions. Firstly, the molecular basis of the underlying genetic defect had been already established in detail at gene and protein level. Secondly, just a single cell type, the tissue macrophage, is primarily implicated in the pathophysiology of the disorder. The rationale for therapeutic intervention of type 1 Gaucher disease is therefore relatively simple: correction (or prevention of ongoing formation) of Gaucher cells. This could either be accomplished by supplementation of macrophages with the enzyme glucocerebrosidase (enzyme replacement therapy), by reduction of glycolipid synthesis with specific inhibitors (substrate deprivation or substrate balancing therapy) or by introduction of glucocerebrosidase cDNA in haematopoietic progenitors of macrophages (gene therapy). The pioneering work of Brady, Barranger and coworkers at the National Institutes of Health (Bethesda, USA) as well as valuable contributions by many others, has led to a highly effective treatment of type 1 Gaucher disease based on chronic intravenous administration of human glucocerebrosidase (see ref. 24-26). Three independent studies of gene transfer to the haematopoietic cells of Gaucher patients have been conducted but none produced encouraging results (see ref. 27). Low transduction efficiencies of CD34 cells and no sustained expression of glucocerebrosidase in white blood cells have contributed to this. The development of gene therapy strategies to correct haematological and genetic disorders has been hampered by the low levels of gene transfer into human stem cells using vectors derived from oncoretroviruses.

Substrate Reduction Therapy

An alternative approach for therapeutic intervention of type 1 Gaucher and other glycosphingolipidoses is substrate deprivation (also termed substrate reduction) therapy. Radin and coworkers firstly formulated the challenging concept (see ref. 28). The approach aims to reduce the rate of glycosphingolipid biosynthesis to levels which match the impaired catabolism. It is conceived that patients who have a significant residual lysosomal enzyme activity could gradually clear lysosomal storage material and therefore should profit most from reduction of substrate biosynthesis (see ref. 29).

Two main classes of inhibitors of glycosphingolipid biosynthesis have presently been described, both of which inhibit the ceramide-specific glucosyltransferase, (also termed glucosylceramide synthase; GlcT-1; UDP-glucose: N-acylsphingosine D-glucosyl-transferase, EC 2.4.1.80). The enzyme catalyses the transfer of glucose to ceramide, the first step of the biosynthesis of glucosphingolipids. The first class of inhibitors is formed by analogues of ceramide. The prototype inhibitor is PDMP (D, L-threo-1-phenyl-2-decanoylamino-3-morpholino-1-propanol). More specific and potent analogues have been subsequently developed based on substituting the morpholino group for a pyrrolodino function and by substitutions at the phenyl group: 4-hydroxy-1-phenyl-2-palmitoylamino-3-pyrrolidono-1-propanol (p-OH—P4) and ethylenedioxy-1-phenyl-palmitoylamino-3-pyrrolidino-1-propanol (EtDo-P4) (see ref. 30). Studies in a knock out mouse model for Fabry disease have shown that oral administration of the compounds can result in a marked reduction of the accumulating glycosphingolipid globotriaosylceramide (see ref. 31).

Iminosugars

The second class of inhibitors of glucosylceramide synthase is formed by N-alkylated iminosugars. Such type of compounds were already in common use as inhibitors of N-glycan processing enzymes and the potential application of N-butyldeoxynojirimycin as HIV inhibitor had been studied in AIDS patients. Platt and Butters at the Glycobiology Institute in Oxford were the first to recognize the ability of N-butyldeoxynojirimycin to inhibit glycosylceramide synthesis at low micromolar concentrations (see ref. 32). The same researchers demonstrated in knock out mouse models of Tay-Sachs disease and Sandhoff disease significant reductions in glycosphingolipid storage in the brain (see ref. 33). Preclinical studies in animals and the previous clinical trial in AIDS patients have indicated (transient) adverse effects in the gastrointestinal tract, probably related to the ability of NB-DNJ to inhibit disaccharidases on the intestinal brush border. Animal studies have shown that the galactose analogue N-butyldeoxygalactonojirimycin (NB-DGJ) may have the same therapeutic efficacy as N-butyldeoxygalactonojirimycin (NB-DNJ) but does not cause gastrointestinal side effects (see ref. 34). Overkleeft and coworkers in their search for inhibitors of glucosidases have serendipitously developed a more potent inhibitor of glucosylceramide synthase. N-Adamantane-1yl-methoxypentyl-deoxynojirimycin (AMP-DNM was found to inhibit glycosphingolipid biosynthesis at nanomolar concentrations (see ref. 35) and able to prevent globotriaosylceramide accumulation in a Fabry knock out mouse model without overt side effects.

The first clinical study of the use of N-butyldeoxynojirimycin (NB-DNJ) to treat a glycosphingolipid storage disorder has been reported recently (Cox et al. 2000). In an open-label phase I/II trial 28 adult type 1 Gaucher patients received three times daily 100 mg NB-DNJ (OGT918; Oxford GlycoSciences).

Improvements in visceromegaly and haematological abnormalities as well as corrections in plasma levels of glucosylceramide and biomarkers of Gaucher disease activity have been described, although the extent of the response is less spectacular than generally observed with high dose enzyme replacement therapy. As expected, a dose-response relationship is demonstrable for NB-DNJ in type 1 Gaucher patients. It was recently reported that administration of three times daily 50 mg NB-DNJ is far less effective (see ref. 37). Very recently the EMEA (the European pendant of the FDA) has registered NB-DNJ (Zavesca, Oxford GlycoSciences) for treatment of type 1 Gaucher patients that are unsuitable to receive enzyme replacement therapy.

Iminosugars and Other Therapeutic Applications

Iminosugars are polyhydroxylated alkaloids that are structural mimics of monosaccharides, where a nitrogen atom replaces the ring oxygen. Examples of iminosugars have been described, for instance, in WO 98102161. As transition charge-state analogues iminosugars may act as inhibitors of enzymes catalyzing the removal or addition of sugars ('glycoconjugate-processing enzymes'). Deoxynojirimycins which are close structural mimics of glucose have been found to be inhibitors of glycoprotein processing alfa-glucosidases I and II. Some N-alkylated deoxynojirimycins, like N-butyl-deoxynojirimycin, have been evaluated as anti-viral (HIV) therapeutics with limited clinical success, despite proven efficacy using in vitro models for viral infectivity (see ref. 38). Presently nonyl-deoxy-galactonojirimycin and N-7-oxanonyl-6-Me-deoxygalactonojirimycin is investigated with regard to therapeutic value for hepatitis virus infections. Other N-alkylated deoxynojirimycins, like N-hydroxyethyl-deoxynojirimycin (Miglitol, Glyset) have been developed for inhibition of intestinal glycosidases. It is assumed that reduction of activity of intestinal glycosidases is beneficial for individuals suffering from insulin resistance (diabetes mellitus type II) since it would buffer the uptake of monosaccharide from food complex carbohydrates. Another use of iminosugars in drug development for metabolic control is in the modification of N-linked oligosaccharides on cell-surface proteins to reduce tumour-cell metastasis (see ref. 39).

It has now been found that abnormal metabolism and abnormal concentrations of glycosphingolipids are associated with a variety of pathological conditions ranging from insulin resistance (diabetes mellitus type II), overweight and obesity, lysosomal storage disorders, inflammation, to hyperpigmentation and skin inflammatory conditions. Moreover, it has been found that glycosphingolipids play an important role in viral, microbial and fungal infections and sensitivity to some endotoxins. We believe that correction of glycosphingolipid metabolism and reduction of excessive glycosphingolipids by administration of carefully selected alkylated iminosugars may result in beneficial responses in such pathological conditions. A prerequisite for the success of such approach is however that the administered compound is effective and well tolerated. It has also been found that iminosugars are able to interfere not only with activity of glucosyltransferases such as glucosylceramide synthase but also with that of various other enzymes (intestinal and other cell surface glycosidases, lysosomal and endosomal glycosidases, glycogen debranching enzyme, and glycoprotein modification glycosidases). Successful therapeutic application of iminosugars therefore requires specificity of biological activities. Essential is insight in the precise nature of glycoconjugate-processing enzyme targets that should be inhibited by a therapeutic iminosugar as well those that should not be inhibited. It forms the basis for developing tailor-made therapeutic iminosugars for different pathological conditions. The presently available iminosugars, however, are far from optimal. Firstly, they are not well bioavailable and relatively poor inhibitors of glucosylceramide synthase. Secondly, they are relatively strong inhibitors of beneficial enzyme activities and consequently cause unacceptable side effects when administered at higher dose. Improvement is therefore required at two different levels: 1, the design and synthesis of novel alkylated iminosugars; and 2, selection of optimal alkylated iminosugars using appropriate criteria of inhibitory activity for each pathological condition.

SUMMARY OF THE INVENTION

The present invention relates to a particular class of novel alkylated iminosugar derivates that can suitably be used for the treatment of various diseases in which the synthesis of glucosylceramide and/or other glycosphingolipids play a role.

Accordingly the present invention relates to a deoxynojirimycin analogue, or a pharmaceutically acceptable salt thereof, having the general structure (1)

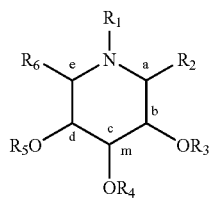

(I)

wherein $R_1$-$R_5$ each independently comprise H or $(CH_2)_n CH_3$ or X;

$R_6$ comprises H, $CH_2OH$ or $CH_2OX$;

M is 0 or 1;

N is 0-9;

a, b, c, d, e are chiral centra having an R or S configuration;

and X comprises a large hydrophobic moiety and a spacer, whereby the hydrophobic moiety is linked through the spacer to the nitrogen atom or carbon atom concerned, and wherein the large hydrophobic moiety is derived from a polycyclic alcohol containing three or more rings each sharing two or more carbon atoms with another ring and is capable of inserting in lipid bilayers.

Figure 2:
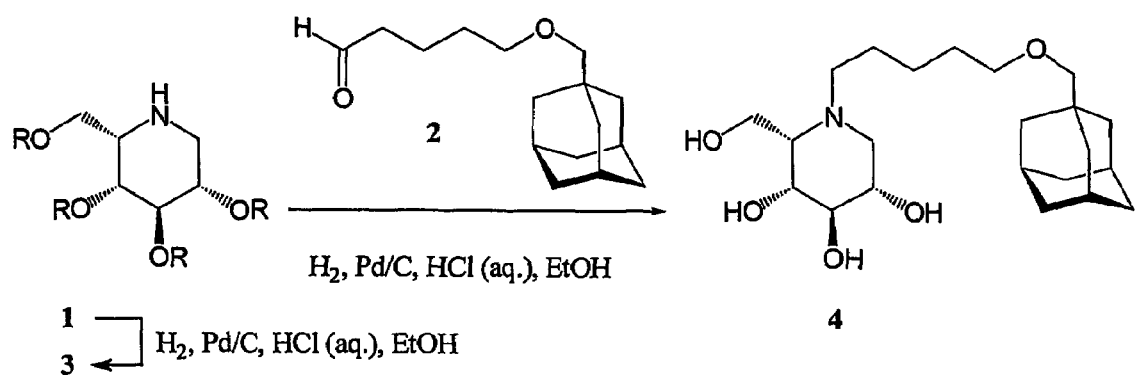

With respect to pyrrolidines (m=0) three ($R_6$=H) or four ($R_6$=$CH_2OH$, $CH_2OX$, see FIG. 2) chiral centra can be discerned. With respect to piperidines (m=1) four ($R_6$=H) or five ($R_6$=$CH_2OH$, $CH_2OX$) chiral centra can be discerned. Depending on the nature and stereochemistry of the individual chiral centra b, c, d and e the pyrrolidines and piperidines mimic natural pentoses (in case $R_6$=H) and hexoses ($R_6$=$CH_2OH$, $CH_2OX$). The nature of the chiral centrum a (in case $R_2$ is not H) defines whether the iminosugar mimics an alpha (a=R)—or a beta (a=S) glycosidic linkage. Specific examples of the deoxynojirimycin analogues according to the present invention are listed below.

| Pyrrolidines ($R_6$ = $CH_2OH$ or $CH_2OX$, m = 0) | |
|---|---|
| a = R, b = S, d = R, e = R | alpha-D-ribofuranoside mimic |
| a = S, b = S, d = R, e = R | beta-D-ribofuranoside mimic |
| a = R, b = R, d = R, e = R | alpha-D-arabinofuranoside mimic |
| a = S, b = R, d = R, e = R | beta-D-arabinofuranoside mimic |
| a = R, b = S, d = S, e = R | alpha-D-xylofuranoside mimic |
| a = S, b = S, d = S, e = R | beta-D-xylofuranoside mimic |
| a = R, b = S, d = R, e = S | alpha-L-lyxofuranoside mimic |
| a = S, b = S, d = R, e = S | beta-L-lyxofuranoside mimic |

| Pyrrolidines ($R_2$ = H, $R_6$ = $CH_2OH$ or $CH_2OX$, m = 0) | |
|---|---|
| b = S, d = R, e = R | alpha-D-1-deoxyribofuranoside mimic |
| b = S, d = R, e = R | beta-D-1-deoxyribofuranoside mimic |
| b = R, d = R, e = R | alpha-D-1-deoxyarabinofuranoside mimic |
| b = R, d = R, e = R | beta-D-1-deoxyarabinofuranoside mimic |
| b = S, d = S, e = R | alpha-D-1-deoxyxylofuranoside mimic |
| b = S, d = S, e = R | beta-D-1-deoxyxylofuranoside mimic |
| b = S, d = R, e = S | alpha-L-1-deoxylyxofuranoside mimic |
| b = S, d = R, e = S | beta-L-1-deoxylyxofuranoside mimic |

| Piperidines ($R_6$ = H, m = 1) | |
|---|---|
| a = S, b = S, c = S, d = R | beta-D-xylopyranoside mimic |
| a = R, b = S, c = S, d = R | alpha-D-xylopyranoside mimic |
| a = S, b = R, c = S, d = R | beta-D-lyxopyranoside mimic |
| a = R, b = R, c = S, d = R | alpha-D-lyxopyranoside mimic |
| a = S, b = S, c = S, d = S | beta-L-arabinopyranoside mimic |
| a = R, b = S, c = S, d = S | alpha-L-arabinopyranoside mimic |

| Piperidines ($R_2$ = H, $R_6$ = H, m = 1) | |
|---|---|
| b = S, c = S, d = R | beta-D-1-deoxyxylopyranoside mimic |
| b = S, c = S, d = R | alpha-D-1-deoxyxylopyranoside mimic |
| b = R, c = S, d = R | beta-D-1-deoxylyxopyranoside mimic |
| b = R, c = S, d = R | alpha-D-1-deoxylyxopyranoside mimic |
| b = S, c = S, d = S | beta-L-1-deoxyarabinopyranoside mimic |
| b = S, c = S, d = S | alpha-L-1-deoxyarabinopyranoside mimic |

| Piperidines ($R_6$ = $CH_2OH$ or $CH_2OX$, m = 1) | |
|---|---|
| a = S, b = S, c = R, d = R, e = R | beta-D-glucopyranoside mimic |
| a = R, b = S, c = R, d = R, e = R | alpha-D-glucopyranoside mimic |
| a = S, b = R, c = R, d = R, e = R | beta-D-mannopyranoside mimic |
| a = R, b = R, c = R, d = R, e = R | alpha-D-mannopyranoside mimic |
| a = S, b = S, c = R, d = S, e = R | beta-D-galactopyranoside mimic |
| a = R, b = S, c = R, d = S, e = R | alpha-D-galacopyranoside mimic |
| a = S, b = S, c = R, d = R, e = S | beta-L-idopyranoside mimic |
| a = R, b = S, c = R, d = R, e = S | alpha-L-idopyranoside mimic |

| Piperidines ($R_2$ = H, $R_6$ = $CH_2OH$ or $CH_2OX$, m = 1) | |
|---|---|
| b = S, c = R, d = R, e = R | beta-D-1-deoxyglucopyranoside mimic |
| b = S, c = R, d = R, e = R | alpha-D-1-deoxyglucopyranoside mimic |
| b = R, c = R, d = R, e = R | beta-D-1-deoxymannopyranoside mimic |
| b = R, c = R, d = R, e = R | alpha-D-1-deoxymannopyranoside mimic |

-continued

Piperidines ($R_2$ = H, $R_6$ = $CH_2OH$ or $CH_2OX$, m = 1)

| | |
|---|---|
| b = S, c = R, d = S, e = R | beta-D-1-deoxygalactopyranoside mimic |
| b = S, c = R, d = S, e = R | alpha-D-1-deoxygalacopyranoside mimic |
| b = S, c = R, d = R, e = S | beta-L-1-deoxyidopyranoside mimic |
| b = S, c = R, d = R, e = S | alpha-L-1-deoxyidopyranoside mimic |

The deoxynojirimycin analogues according to the present invention comprise at least one entity X that comprises a hydrophobic moiety and a spacer. The entity X can be located at any of the positions $R_1$, $R_2$, $R_3$, $R_4$, $R_5$, $R_6$.

The spacer and the hydrophobic moiety can suitably be represented by Z and Y as shown in FIG. 1.

Preferably, the large hydrophobic moiety is linked to said nitrogen atom of the deoxynojirimycin by means of a spacer comprising an alkoxy polyalkylene or polyalkylene chain of from 3 to 8 carbon atoms. More preferably, the large hydrophobic moiety is derived from a compound selected from the group consisting of adamantanemethanol, cholesterol, β-cholestanol, adamantanol and 9-hydroxyphenanthrene.

The word 'spacer' refers to any bivalent moiety or group capable of linking a hydrophobic group to the N atom of deoxynojirimycine.

Preferably the deoxynojirimycin analogues according to the present invention have the ido-configuration. In particular ido-N-(5-adamantane-1-yl-methoxy-pentyl)deoxynojirimycin is a preferred compound.

The preparation of the deoxynojirimycin analogues according to the present invention is exemplified by the following examples.

N-(adamantane-1-yl-methoxypentyl)-L-ido-deoxynojirimycin 4

2,3,4,6-tetra-O-benzyl-L-ido-deoxynojirimycin 1 (Tetrahedron Lett. 44, 3085-3088, 2003) was debenzylated via hydrogenation ($H_2$, Pd/C, HCl (aq.), EtOH) to 3, which was condensed with adamantane-1-yl-methoxypentanal 2 (J. Biol. Chem. 273, 26522, 1998, WO 98102161) under reductive amination conditions ($H_2$, Pd/C, HCl (aq.), EtOH) to afford N-(adamantane-1-yl-methoxypentyl)-L-ido-deoxynojirimycin 4. Purification provided homogeneous target compound 4 in 93% yield as a light yellow syrup (see FIG. 2).

N-(adamantane-1-yl-methoxypentyl)-D-galacto-deoxynojirimycin 7

The synthesis of 7 was accomplished (see FIG. 3) following the synthetic route as outlined above for the ido-congener 4, starting form 2,3,4,6-tetra-O-benzyl-D-galacto-nojirimycin 7 (Tetrahedron 56, 32, 5819-5834, 2000).

C1-beta-(adamantane-1-yl-methoxypentyl)-deoxynojirimycin 17. N-methyl-C1-beta-(adamantane-1-yl-methoxypentyl)-deoxynojirimycin 18 and N-butyl-C1-beta-(adamantane-1-yl-methoxypentyl)-deoxynojirimycin 19.

Figure 4:
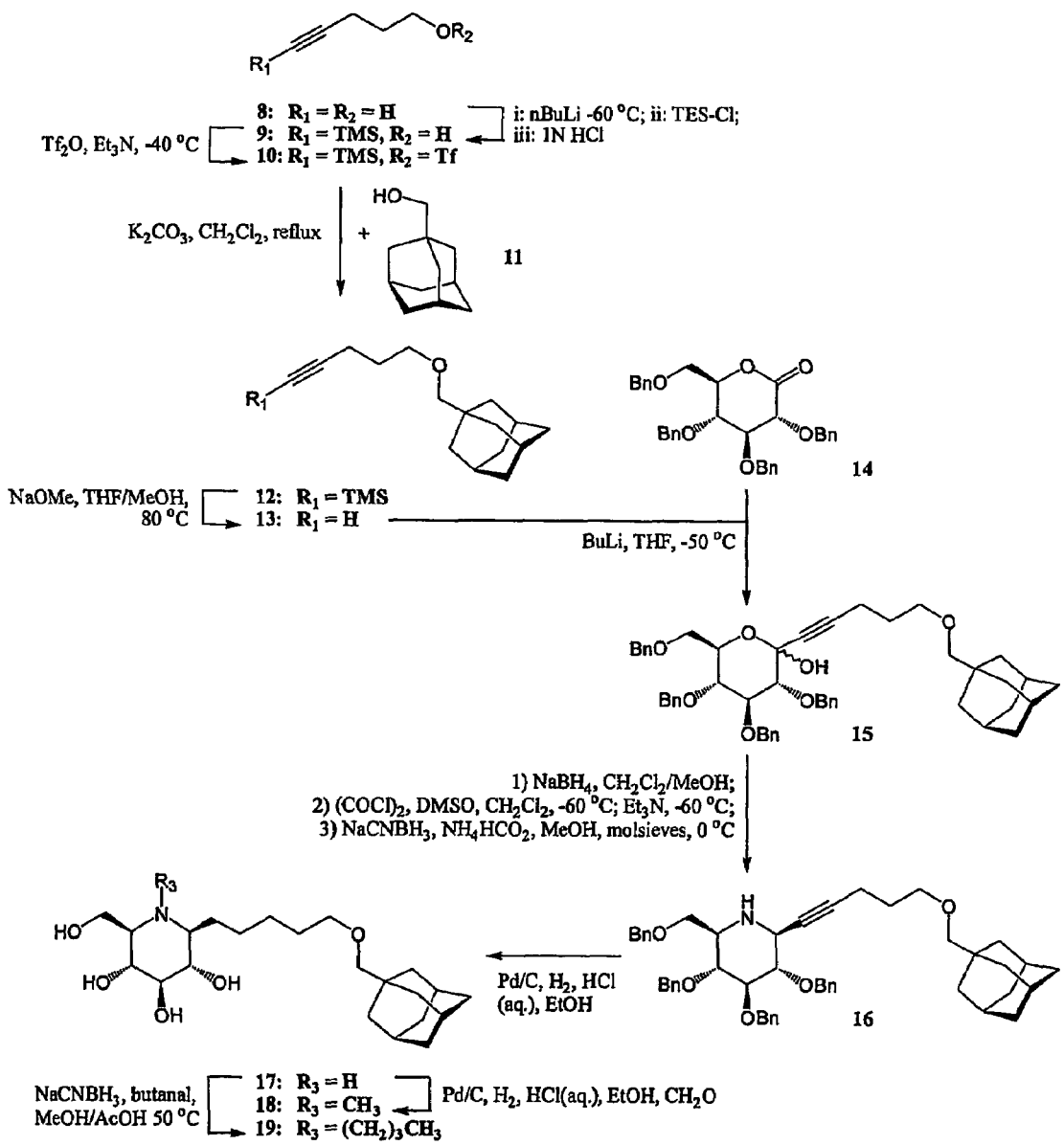

The synthesis of beta-C1-alkyldeoxynojirimycin derivatives 17, 18 and 19 commences with the preparation of 5-O-(adamantane-1-methyl)-1-pentynol 13 (see FIG. 4). Pentyn-1-ol 8 was fully sylylated (nBuLi, TMSCl) followed by selective deprotection of the silyl-ether (1N HCl) to provide protected acetylene 9. The free alcohol of 9 was transformed into trifluoromethanesulfonyl ester 10 (trifluoromethanesulfonylchloride, triethylamine). Alkylation of adamantanemethanol 11 with 10 ($K_2CO_3$, refluxing $CH_2Cl_2$) and subsequent removal of the TMS protective group (sodiummethanolate, MeOH/THF) afforded acetylene 13 in 64% overall yield based on 8. Nucleophillic addition of the lithiate of 13 (prepared by reacting it with butyllithium in THF at −50° C.) to 2,3,4,6-tetra-O-benzyl-D-gluconic-delta-lactone 14 (J. Org. Chem., 2531, 1967) afforded ketoglucoside 15 as an anomeric mixture. Compound 15 was readily, and with high stereoselectivity, transformed into the fully protected iminosugar 16 using the following three step procedure (Eur. J. Org. Chem. 5, 1185-1189, 1999): 1) reduction to the corresponding diol ($NaBH_4$, $CH_2Cl_2$/MeOH), 2) oxidation to the diketo compound (Swern oxidation) and 3) double reductive amination employing ammonium formate and sodium cyanoborohydride (overall yield based on 14 was 45%). Palladium-catalysed hydrogenation afforded iminosugar 17 (79%), from which the methyl- and butyl homologues 18 and 19 were readily prepared by reductive amination with formaldehyde (18, 20% yield) and butanal (19, 73% yield), respectively.

2-O-(adamantane-1-yl-methoxypentyl)-deoxynojirimycin 28, N-methyl-2-O-(adamantane-1-yl-methoxy-pentyl)-deoxynojirimycin 29 and N-butyl-2-O-(adamantane-1-yl-methoxy-pentyl)-deoxynojirimycin 30

The preparation of 2-O-alkylated deoxynojirimycin derivatives 28, 29 and 30 (see FIG. 5) starts with the p-methoxybenzyl-protection of the free alcohol function in allyl-3,4,6-tri-O-benzyl-β-D-glucopyranoside 20 (Tetrahedron: Asymmetry, 8, 765-774, 1997) and subsequent isomerization/hydrolysis of the anomeric allyl-group to provide 22 in 80% over two steps. The hemi-acetal 22 was transformed into the orthogonally protected deoxynojirimycin derivative 23 using the following four step procedure: 1) reduction to the corresponding diol ($LiAlH_4$, THF), 2) oxidation to the aldehydoketone (Swern oxidation), 3) double reductive amination employing ammonium formate and sodium cyanoborohydride and 4) protection of the resulting secondary amine with the benzyloxycarbonyl group (ZCl, $K_2CO_3$, 71% over the four steps). Treatment of 23 with 2% TFA afforded compound 24 (99% yield), with the C-2-OH selectively deprotected for ensuing alkylation. The corresponding alkylating agent 1-bromo-5-(adamantane-1-yl)methoxypentane 26 was prepared from aldehyde 2 through reduction of the aldehyde function to the corresponding primary alcohol ($NaBH_4$, MeOH) followed by bromination under the agency of $PBr_3$ (88%, two steps). Alkylation of 24 was effected by addition of excess 26 and treatment with sodium hydride in DMF to furnish 27 in 83%. Reductive removal of the Z- and benzyl protective groups in 27 afforded iminosugar 28 (80% yield), from which the methyl- and butyl homologues 29 and 30 were readily prepared by reductive amination with formaldehyde (29, 49% yield) and butanal (30, 79% yield), respectively.

Spectroscopic Data:

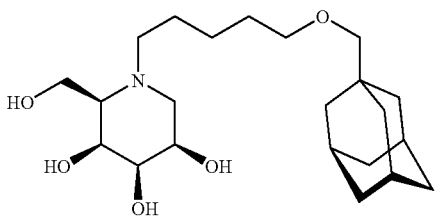

N-(adamantane-1-yl-methoxypentyl)-L-ido-deoxy-nojirimycin (4): $^1$H-NMR (MeOD, 400 MHz): δ 4.01-3.97 (dd, 1H, H6), 3.89 (m, 1H, H2), 3.85-3.70 (m, 3H, H2, H3, H4), 3.55-3.52 (m, 2H, CH$_2$ spacer), 3.40-3.08 (m, 5H, 2*H1, H5, CH$_2$ spacer), 2.96 (s, 2H, O—CH$_2$ methoxy), 1.94 (broad s, 3H, CH adamantyl), 1.77-1.66 (broad dd, 6H, 3*CH$_2$ adamantyl), 1.63-1.54 (d, 4H, 2*CH$_2$ spacer), 1.55 (d, 6H, 3*CH$_2$ adamantyl), 1.45-1.37 (m, 2H, middle CH$_2$ spacer). MS (ESI): obs. m/z=398.2 [M+H]$^+$; Calculated MW for C$_{22}$H$_{39}$NO$_5$: 397.3.

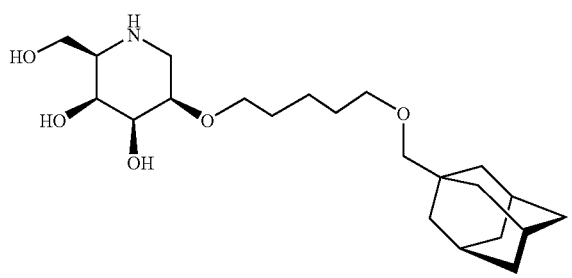

2-O-(adamantane-1-yl-methoxypentyl)-deoxy-nojirimycin (28): $^1$H-NMR (MeOD, 400 MHz): δ 3.92-3.84 (2*dd, 2H, 2*H6), 3.72-3.62 (m, 2H, O—CH$_2$ spacer), 3.57-3.43 (m, 3H, H2, H3, H4), 3.38-3.36 (m, 2H, O—CH$_2$ spacer), 3.07 (m, 1H, H5), 2.95 (s, 2H, O—CH$_2$ methoxy), 2.89-2.79 (m, 2H, 2*H1), 1.93 (broad s, 3H, CH adamantyl), 1.76-1.65 (broad dd, 6H, 3*CH$_2$ adamantyl), 1.62-1.56 (d, 4H, 2*CH$_2$ spacer), 1.54 (d, 6H, 3*CH$_2$ adamantyl), 1.45-1.39 (m, 2H, middle CH$_2$ spacer). MS (ESI): obs. m/z=398.2 [M+H]$^+$; Calculated MW for C$_{22}$H$_{39}$NO$_5$: 397.3.

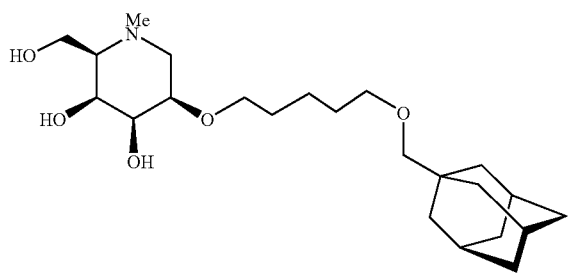

N-Methyl-2-O-(adamantane-1-yl-methoxypentyl)-deoxy-nojirimycin (29): $^1$H-NMR (MeOD, 400 MHz): δ 4.13-4.10 (2*broad d, 2H, 2*H6), 3.72-3.64 (m, 2H, O—CH$_2$ spacer), 3.62-3.48 (m, 3H, H2, H3, H4), 3.42-3.38 (m, 2H, O—CH$_2$ spacer), 3.09-2.89 (m, 3H, H5 and 2*H1), 3.01 (s, 3H, N—CH$_3$), 2.95 (s, 2H, O—CH$_2$ methoxy), 1.96 (broad s, 3H, CH adamantyl), 1.78-1.65 (broad dd, 6H, 3*CH$_2$ adamantyl), 1.62-1.56 (d, 4H, 2*CH$_2$ spacer), 1.57 (d, 6H, 3*CH$_2$ adamantyl), 1.48-1.42 (m, 2H, middle CH$_2$ spacer). MS (ESI): obs. m/z=412.2 [M+H]$^+$; Calculated MW for C$_{23}$H$_{41}$NO$_5$: 411.3.

N-Butyl-2-O-(adamantane-1-yl-methoxypentyl)-deoxy-nojirimycin (30):

MS (ESI): obs. m/z=454.2 [M+H]$^+$; Calculated MW for C$_{26}$H$_{47}$NO$_5$: 453.3.

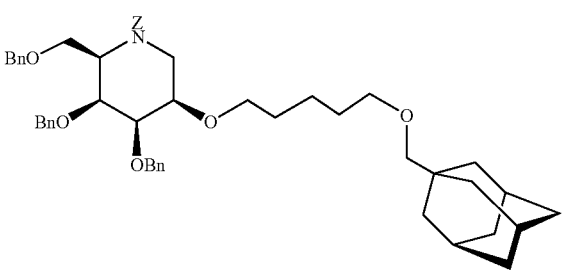

N-benzyloxycarbonyl-2-O-(adamantane-1-yl-methoxypentyl)-3,4,6-tri-O-benzyl-deoxy-nojirimycin (27): $^1$H-NMR (CDCl$_3$, 400 MHz): δ 7.31-7.25 (m, 20H, CH Bn), 5.16-5.06 (2H, CH$_2$ Bn), 4.75-4.49 (2*CH$_2$ Bn), 4.43-4.31 (2H, CH$_2$ Bn), 4.14-4.12 (m, 1H, H5), 4.00-3.97 (dd, 1H, H1 ax or eq), 3.93-3.89 (dd, 1H, H4), 3.67-3.54 (m, 4H, H2, H3, 2*H6), 3.38-3.31 (m, 5H, H1 ax or eq, 2*O—CH$_2$ spacer), 2.93 (s, 2H, CH$_2$ methoxy), 1.94 (broad s, 3H, CH adamantyl), 1.71-1.62 (broad dd, 6H, 3*CH$_2$ adamantyl), 1.58-1.52 (m, 10H, 3*CH$_2$ adamantyl, 2*CH$_2$ spacer), 1.38-1.33 (m, 2H, middle CH$_2$ spacer). $^{13}$C-NMR (CDCl$_3$, 100 MHz): δ 155.7 (C=O, Z-group), 138.3, 136.6 (C$_q$ Bn and Z), 128.4-127.4 (CH arom. Bn), 82.4, 79.5, 74.3 (3*CH, C2, C3 and C4), 73.1, 72.9, 72.8, 71.5, 69.0, 68.5, 67.1 (7*CH$_2$, 3*CH$_2$ Bn, CH$_2$ Z-group, 2*O—CH$_2$ spacer, C6), 55.8 (C5), 41.6 (C1), 39.7, 37.2 (2*CH$_2$ adamantyl), 34.0 (C$_q$ adamantyl), 29.7, 29.4 (2*CH$_2$ spacer), 28.2 (CH adamantyl), 22.7 (middle CH$_2$ spacer). MS (ESI): obs. m/z=802.4 [M+H]$^+$; 824.6 [M+Na]$^+$; Calculated MW for C$_{51}$H$_{63}$NO$_7$: 801.5.

Fields of Application

1. Diabetes Melltus Type II (Insulin Resistance)

The incidence of diabetes mellitus type II is dramatically increasing in the Western World. The primary underlying defect is an impaired uptake of glucose from the bloodstream by muscle and adipose tissue as the result of a reduced sensitivity to mobilize GLUT4 transporters to their cell surface in response to insulin. It is already known for many years that increased concentrations of fatty acids in muscle are associated with aberrant glucose homeostasis. Conversely, the improvements of glucose homeostasis induced by PPAR gamma agonists and rexinoids are associated with altered partitioning of fatty acids, i.e. redistribution of fatty acids to adipose tissue and relative depletion of muscle fatty acid uptake and metabolism. Poorly understood, however, is the molecular mechanism by which lipotoxicity in the muscle causes onset and progression of diabetes. Further insight in this matter will therefore assist in improving/developing medicaments for treating insulin resistance.

Molecular Mechanism of Lipopathogenesis

Research activities on glycosphingolipids and diabetes type II in the Department of Biochemistry at the Academic Medical Center/University of Amsterdam has recently led to an unexpected new insight in the lipopathogenesis of diabetes mellitus type II. The underlying mechanism is described in detail below.

Role for Glycosphingolipids in Acquired Insulin Resistance

A role was hypothesized for (glyco)sphingolipids in the pathogenesis of diabetes. This thought stems from the ignored fact that palmitate is the essential building block of the ceramide moiety in sphingolipids: the first step of their biosynthesis involves the transfer of palmitate to serine, catalyzed by serine palmitoyltransferase, see FIG. 1. The rate of synthesis of sphingolipids in the liver is highly dependent on the concentration of palmitate. Importantly, this could be experimentally confirmed for cultured muscle cells (smooth muscle cells, myoblasts): addition of 0.1, 0.5, 1.0 mM palmitate in the culture medium led to proportional increases in the synthesis of glycosphingolipids, as revealed by increased incorporation of radio-labelled serine in these structures.

This finding prompted a more detailed examination of the possibility that actually (glyco)sphingolipids mediate the lipotoxicity in muscles that underlies diabetes. It has recently been evidenced that GM3 (the most simple ganglioside at the cell surface, see FIG. 2) may impair insulin signalling. In this respect it is observed that the concentration of GM3 at the cell surface appears to regulate the uptake of glucose in response to insulin by negatively interfering with multi-clustering of insulin receptors. Moreover, high concentrations of GM3 are associated with reduced mobilization of GLUT4 to the cell surface. Conversely, reduction of GM3 is associated with enhanced insulin sensitivity (see Yamishita et al. Proc Natl Acad Sci USA (2003) 100, 3445-9 Enhanced insulin sensitivity in mice lacking ganglioside GM3; Tagami et al. (2002) J Biol Chem 277,3085-92 Ganglioside GM3 participates in the pathological conditions of insulin resistance). We postulate that at obese conditions, palmitate levels are chronically high and that therefore the formation of glucosphingolipids in adipocytes as well as muscle cells will occur at increased rates, favouring insulin resistance. The connection between increased concentration of palmitate in muscle as driving force for the increased local glycosphingolipid synthesis (including GM3) and insulin resistance (see FIG. 3) has not yet been recognised by others.

Crucial Role of Glucosylceramide Synthase

Figure 3:
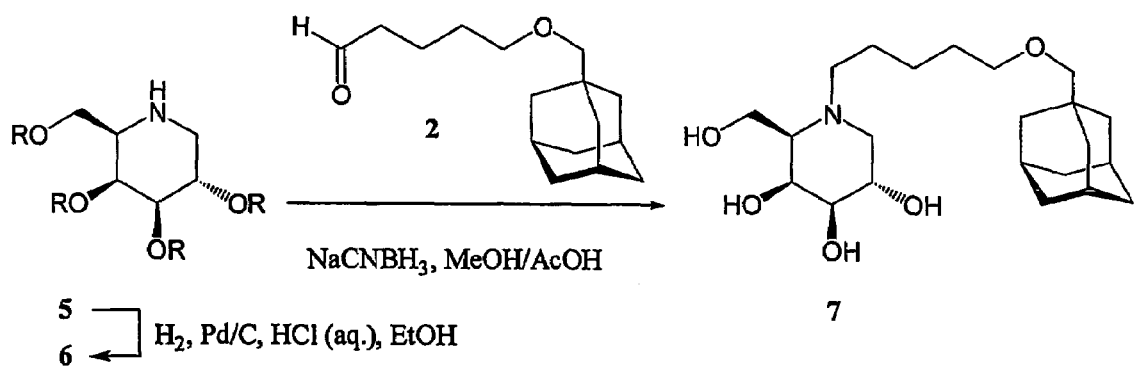

Further it was realised that the concentration of GM3 and other gangliosides at the cell surface is highly dependent on the activity of glucosylceramide synthase (the synthesis of glucosylceramide), the rate limiting step in ganglioside synthesis (see FIG. 3). This enzyme catalyzes the formation of glucosylceramide from ceramide and UDP-glucose. The Km values of both its substrates (ceramide and UDP-glucose) are in the physiological range. We show that glucosylceramide synthase is a key regulatory enzyme with respect to insulin sensitivity. Increases in its activity have been observed and reported previously in response to inflammatory cytokines (TNF-alfa), steroid hormones, saturated fatty acid, and viral infection. It has now surprisingly been found that the changes in glycosphingolipid synthesis have an impact on the promotion of diabetes mellitus type II (see FIG. 4). This finding that lipopathogenesis impacts diabetes type II shows that inhibition of glucosylceramide synthase activity exerts a beneficial, anti-hyperglycaemic effect.

Novel Use of Iminosugar-Based Inhibitors

It has become clear that deoxynojirimycins, a particular category of iminosugars, are suitable agents to reduce glycosphingolipid synthesis by the inhibition of the synthesis of glucosylceramide. Further, considerable hands-on expertise has been obtained with the safety of iminosugar administration in man.

N-butyl-deoxynojirimycin has been recently registered as drug for the treatment of type 1 Gaucher disease. A clinical study, largely undertaken at the Academic Medical Center in collaboration with the University of Cambridge, revealed that the drug is tolerated in the majority of patients, at least up to 5 years. Despite the fact that glycosphingolipid synthesis is only very moderately (20-30%) inhibited by 100 mg TID N-butyl-deoxynojirimycin, some Gaucher patients however develop serious intestinal complaints and occasionally alarming peripheral neuropathy. At higher doses of N-butyl-deoxynojirimycin these adverse events occur even more frequently. We postulate that the poor specificity of N-butyl-deoxynojirimycin with respect to inhibition of glucosidases and glucosyltransferases contributes to these undesired side-effects. As shown in Table 1, N-butyl-deoxynojirimycin is also a very potent inhibitor of intestinal glycosidases. We postulate that this inhibiting effect results in at least part of the intestinal complaints of patients. It is an inhibitor of lysosomal alfa-glucosidase and glucocerebrosidase. We postulate that this effect results in the associated risk for pathological intralysosomal accumulation of glycogen and glucocerebroside in lysosomes. At concentrations required to significantly lower GM3 in (pre)diabetic persons, adverse events will undoubtedly occur when use is made of N-butyl-deoxynojirimycin.

Design of Specific Inhibitors as Therapeutic Agents for Insulin Resistance (Diabetes Mellitus Type II)

N-(5-adamantane-1-yl-methoxy-pentyl)deoxynojirimycin (formerly also known as AMP-DNM) shows a number of attractive features for its use as therapeutic agent for diabetes mellitus type II: the compound is highly bioavailable when orally administered; the compound is a potent inhibitor of glucosylceramide synthase; the compound is metabolically inert and shows no intrinsic cellular toxicity at doses envisioned during therapy.

However, based on observations made with in vitro enzyme activity assays and with cultured cells, it appears possible that chronic administration of N-(5-adamantane-1-yl-methoxy-pentyl)deoxynojirimycin could also affect other metabolic pathways. For example, potential inhibition of lysosomal glycosidase alfa-glucosidase and of lysosomal glucocerebrosidase following long term administration of N-(5-adamantane-1-yl-methoxy-pentyl)deoxynojirimycin can not be entirely excluded. This might lead to intralysosomal accumulation glycogen or glucosylceramide, respectively. Excessive lysosomal storage of glycogen or glucosylceramide might result in pathology that resembles Pompe and Gaucher disease, respectively. Furthermore, N-(5-adamantane-1-yl-methoxy-pentyl)deoxynojirimycin is also an inhibitor of intestinal sucrase and as such might cause gastrointestinal complications. A potent inhibition of intestinal glycosidase would lead to accumulation of osmotic active sugars in the gastrointestinal lumen and favour enterobacterial growth, both contributing to spasms and diarrhoea. Such complications would affect compliance and would reduce application of N-(5-adamantane-1-yl-methoxy-pentyl)deoxynojirimycin in practice.

All these considerations led us to search for an iminosugar structure that still harbours the desired properties of N-(5-adamantane-1-yl-methoxy-pentyl)deoxynojirimycin but lacks its unfavourable features with regard to chronic treatment of insulin-resistant individuals.

The Following Two Selection Criteria Were Applied:

1. Reduced inhibition of lysosomal glycosidases: β-glucosidase and glucocerebrosidase.

In this respect it is observed that inhibition of lysosomal glycosidases by an iminosugar is not desired since it may only increase the risk for pathological intralysosomal storage of metabolites, mimicking lysosomal storage disorders.

2. Lack of inhibition of intestinal glycosidases.

Another approach to intervene in diabetes mellitus type II is based on buffering the uptake of food-derived saccharide in the gastrointestinal tract by inhibition of intestinal glycosidases. Synthetic inhibitors of sucrase (Acarbose, N-hydroxyethyl-deoxynojirimycin) are based on this concept and are registered antidiabetic drugs.

N-hydroxyethyl-deoxynojirimycin is the most potent antidiabetic agent of the sucrase inhibitors (Campbell L, Baker D E & Campbell R K, Ann Pharmacother 2000;34: 1291-1301). The big disadvantage of potent synthetic inhibitors of intestinal glycosidase like N-hydroxyethyl-deoxynojirimycin and Acarbose is, however, that they can cause inevitably severe intestinal complaints. The potent intestinal glycosidase inhibitors N-hydroxyethyl-deoxynojirimycin and Acarbose are therefore not very well tolerated by many individuals, resulting in a poor compliance and limited application.

Although N-hydroxyethyl-deoxynojirimycin and Acarbose exert beneficial effects, we have realised that it is actually questionable whether this is related to their ability to inhibit intestinal glycosidases. Interestingly, administration of N-hydroxyethyl-deoxynojirimycin or Acarbose results even in the absence of carbohydrate-rich food in reduction of blood glucose levels. This is inconsistent with the presumed mode of therapeutic action of the compounds. It seems more likely that after uptake in the body N-hydroxyethyl-deoxynojirimycin and (metabolites of) Acarbose rather act beneficially by inhibiting glucosylceramide synthase. This implies that inhibition of intestinal glycosidases is not a prerequisite for their therapeutic effects but only leads to undesired side effects.

Based on the selection criteria described above, ido-configuration of N-(5-adamantane-1-yl-methoxy-pentyl)deoxynojirimycin was identified as an attractive iminosugar for the treatment of insulin-resistance (diabetes mellitus type II). Table 1 shows that ido-N-(5-adamantane-1-yl-methoxy-pentyl)deoxynojirimycin, as compared to N-(5-adamantane-1-yl-methoxy-pentyl)deoxynojirimycin, is not inhibiting lysosomal glucocerebrosidase and only poorly inhibits β-glucosidase activity. Furthermore, ido-N-(5-adamantane-1-yl-methoxy-pentyl)deoxynojirimycin is a poor inhibitor of intestinal glycosidases. Importantly, ido-N-(5-adamantane-1-yl-methoxy-pentyl)deoxynojirimycin is still a potent inhibitor of glucosylceramide synthase when tested on cultured cells (see Table 2).

TABLE 2

| | In vivo IC50 value (uM) for inhibition of: | |
|---|---|---|
| Iminosugar | GCsynthase | GlcCer-ase |
| N-(5-adamantane-1-yl-methoxy-pentyl)deoxynojirimycin | 0.25 | 0.8 |
| Ido-N-(5-adamantane-1-yl-methoxy-pentyl)deoxynojirimycin | 2.5 | >100 |

The value of ido-N-(5-adamantane-1-yl-methoxy-pentyl) deoxynojirimycin as anti-hyperglycaemic agent was subsequently analysed in animal models exactly according to the procedures described above for N-(5-adamantane-1-yl-methoxy-pentyl)deoxynojirimycin. For this purpose animals were daily fed with ido-N-(5-adamantane-1-yl-methoxy-pentyl) deoxynojirimycin at different concentrations. At a dose of 250 mg ido-N-(5-adamantane-1-yl-methoxy-pentyl)deoxynojirimycin/kg similar beneficial effects to 25 mg N-(5-adamantane-1-yl-methoxy-pentyl)deoxynojirimycin/kg were noted.

Role of Glycosphingolipids in Obesity

We have found that the increasing consumption of animal fat (rich in palmitate) and simple sugars (mono- and disaccharides) favours overproduction of glycosphingolipids. High levels of glycosphingolipids inhibit hormones involved in energy homeostasis, for example insulin. High glycosphingolipid levels reinforce the misbalance between energy intake and expenditure and favours ongoing gain of weight and associated co-morbidities. This novel insight opens a new avenue for therapeutic intervention: the use of iminosugars that can reduce overproduction of glycosphingolipids in individuals with overweight and obesity. Accordingly, the deoxynojirimycin analogues, or pharmaceutically acceptable salts thereof, according to the present invention can suitably be used for the treatment of overweight and obesity.

Selection of Alkylated Iminosugars to Treat Overweight and Obesity

In particular ido-N-(5-adamantane-1-yl-methoxy-pentyl) deoxynojirimycin was found to be ideally suited compound for this purpose. It is well bioavailable, show no cellular toxicity at envisioned dosages and are relatively specific inhibitors of glucosylceramide synthase. The advantage of ido-N-(5-adamantane-1-yl-methoxy-pentyl)deoxynojirimycin is that it does not cause gastrointestinal complaints, a complication caused by most iminosugars. The absence of such side effects will improve compliance.

TABLE 1

| | In vitro IC50 value (uM) for inhibition of: | | | | |
|---|---|---|---|---|---|
| Iminosugar | GCsynthase | GlcCer-ase | Alfa-Glu-ase | Sucrase | Maltase | Lactase |
| N-(5-adamantane-1-yl-methoxy-pentyl)deoxynojirimycin | 15 | 0.4 | 0.1 | 4.5 | >25 | 18 |
| Ido-N-(5-adamantane-1-yl-methoxy-pentyl)deoxynojirimycin | 150 | >100 | 11 | >100 | >100 | >100 |

2. Overweight and Obesity

Throughout the world, the prevalence of overweight and obesity has taken on epidemic proportions. In the Netherlands, as elsewhere, there is a steady rise in the number of individuals suffering from overweight and obesity. While it is comparable to the situation in other European countries, this increase is less pronounced than in the United Kingdom and Germany, for example. Most staggering is the increased prevalence in the United States. On average, 40% of Dutch adults are overweight, while 10% of the adult population is obese. It is estimated that 1 to 1.5% of adults suffer from morbid obesity. In 2000 in the United States 56% of adults were overweight, 20% obese and 2.3% morbidly obese. According to the WHO definition, adults are defined as obese (severely overweight) if they have a BMI of 30 kg/m$^2$ or more. Those with a BMI value of between 25 and 30 kg/m$^2$ are said to be overweight. The BMI (Body Mass Index) is defined as an individual's body weight (in kg) divided by the square of their height (in meters).

One of the first consequences of weight gain is insulin resistance, which disrupts the normal action of insulin. Insulin resistance plays a key role in the development of metabolic syndrome. This syndrome is characterised by a number of associated metabolic anomalies such as insulin resistance, dyslipidaemia (low HDL serum cholesterol, high serum triglycerides, high LDL serum cholesterol), hypertension, and abdominal obesity. These anomalies in turn form the basis for the development of disorders such as type II diabetes mellitus (age-related diabetes) and its complications. Other health risks that are associated with overweight and obesity are: cardiovascular diseases, various types of cancer, gall-bladder diseases, arthrosis, respiratory problems, gout, infertility, menstrual disorders and foetal defects. The greater the overweight the greater the risk of such comorbidity. Of all these health risks, the increased prevalence of glucose intolerance and type II diabetes mellitus, is particularly worrying. In the United States this is even occurring in children. Recent studies revealed that about 60% of obese children (5-17 years) showed additional risk factors for cardiovascular disease. Glucose intolerance was observed in 25% of 55 obese children (4-10 years) and 21% of 112 teenagers (11-18 year). In addition, obesity is often accompanied by psychological and social problems, as well as a reduced quality of life. The morbidity associated with obesity (and, to a lesser extent, with overweight) leads to numerous (medicinal) treatments and additional work disability, as well as increased costs for the health care. It is estimated that in the United States the cost of health care directly related to overweight and obesity are 6-7% of total, the indirect costs are estimated to be four-fold higher.

3. Lysosomal Storage Disorders

Inherited disorders characterised by intralysosomal accumulation of glucosphingolipids (GM1 gangliosidosis, Sandhoff disease (GM2 gangliosidosis, type II or variant O), Tay-Sachs disease (GM2 gangliosidosis, type I or variant B), Fabry disease (a-galactosyl-lactosylceramidosis), lactosylceramidosis, Gaucher disease (glucocerebrosidosis) form a large fraction of all diagnosed inborn of metabolism in the Western World. It has been previously envisioned that patients suffering from these diseases should benefit from a reduction of synthesis of the accumulating glucosphingolipids. Recently N-butyl-deoxynojirimycin has been registered for the treatment of type 1 Gaucher disease by means of so called substrate reduction therapy (SRT).

The clinical experience with N-butyl-deoxynojirimycin has learned that the application of the compound is limited by the poor features of this iminosugar. N-butyl-deoxynojirimycin is poorly effective since it is only poorly bioavailable and it is a relatively poor inhibitor of glucosylceramide synthase. On the other hand, N-butyl-deoxynojirimycin causes serious side effects at higher doses due to its ability to markedly inhibit lysosomal and intestinal glycosidases.

A Specific Deoxynojirimycin Derivative for SRT of Glucosphingolipidoses: IDO-N-(5-Adamantane-1-yl-Methoxy-Pentyl)Deoxynojirimycin We have found that more optimal iminosugars for SRT of glucosphingolipid storage disorders can be designed. Compounds were selected on the basis of their potency of inhibiting glucosylceramide synthase and inability to inhibit activities of lysosomal and intestinal glycosidases. Tables 3 and 4 reveal that ido-N-(5-adamantane-1-yl-methoxy-pentyl)deoxynojirimycin is an ideal substance that shows superior features compared to N-butyl-deoxynojirimycin.

TABLE 3

Apparent in vitro IC50 values (uM) for lysosomal glycosidases

| Iminosugar | Hexosaminidase | A-Galactosidase | A b-Galactosidase | Glucocerebrosidase | a-Glucosidase |
| --- | --- | --- | --- | --- | --- |
| N-butyl-deoxynojirimycin | >100 | >100 | >100 | 500 | 0.8 |
| Ido-N-(5-adamantane-1-yl-methoxy-pentyl)deoxynojirimycin | >100 | >100 | >100 | >100 | 11 |

Enzyme activities were measured with appropriate 4-MU substrates using purified enzymes from spleen. IC50 values for determined by assessment of the amount of iminosugar required for 50% inhibition of enzyme activity.

TABLE 4

In vivo IC50 value for glucosylceramide synthase

| Iminosugar | IC50 (uM) |
| --- | --- |
| N-butyl-deoxynojirimycin | 35 |
| Ido-N-(5-adamantane-1-yl-methoxy-pentyl)deoxynojirimycin | 2.5 |

In vivo glucosylceramide synthase activity was determined according to the procedure described in J. Biol. Chem, 273, 26522-27 (1998). Briefly, glucosylceramide synthase activity was measured by exposing cells to fluorescent C6-NBD-ceramide complexed to albumin. The conversion of C6-NBD-ceramide to C6-NBD-glucosylceramide was analysed following harvesting of cells, lipid extraction and quantitative thin layer chromatography.

4. Inflammatory Diseases

Inflammation is accompanied by local tissue destruction and associated clinical symptoms. Chronic inflammation is a particular harmful process. Such type of inflammation is often driven by chronically activated macrophages. Various pharmacological agents are used to treat inflammation and chronic inflammation. However, these agents are either not optimally effective or exert serious side effects. There is a need for improved anti-inflammatory agents based on a distinct mode of action.

Role of Glycosphingolipids in Inflammation

It has now been found that inflammation, especially chronic inflammation, is associated with overproduction of glycosphingolipids and that this overproduction enforces the inflammatory state of macrophages and thus promotes the cascade of tissue inflammation. Increased glycosphingolipid levels activate macrophages in two manners. Firstly, excessive degradation of glucosylceramide by the non-lysosomal glucosylceramidase results in formation of ceramide that acts as signalling molecule. Moreover, part of the ceramide is metabolised to diacylglycerol that stimulates PKC. The production of ceramide and diacylglycerol both favour ongoing activation of macrophages. Secondly, increased synthesis of glycosphingolipids during inflammation changes the glycosphingolipid composition of rafts at the cell surface. This affects normal cell behaviour and promotes inflammatory processes.

A New Class of Anti-Inflammatory Agents

The above findings allowed us to envision that iminosugars should be useful anti-inflammatory agents that act via a novel mode of action. Based on the desired features ido-N-(5-adamantane-1-yl-methoxy-pentyl)deoxynojirimycin was selected as ideally suited anti-inflammatory agent. This compound is well bioavailable, shows no cellular toxicity at envisioned dosages and is well tolerated. The compound is a potent inhibitors of the non-lysosomal glucosylceramidase and glucosylceramide synthase, both enzyme activities that contribute to the severity and chronic nature of inflammation. Accordingly, the deoxynojirimycin analogues, or pharmaceutically acceptable salts thereof, can suitable be used for the treatment of inflammatory diseases.

5. Hyperpigmentation and Inflammatory Skin Conditions

Pigmentation

Humans produce two types of the pigment melanin: the brown/black type, or eumelanin; and the amber/red type, or pheomelanin. Eumelanin is primarily responsible for the colour seen in skin, hair and eyes. Synthesis of melanin occurs in specific compartments of specialized cells, the melanosomes of melanocytes. The pigment is subsequently transferred to the keratinocytes in the skin.

Pigmentation usually increases with age and may be altered by genetic defects or by acquired diseases. In some cases, this means an increase in pigmentation (hyperpigmentation); in some cases, it means less colour (hypopigmentation). Several types of hyperpigmentation occur: 1, freckles; 2, pregnancy-related hyperpigmentation; 3, hyperpigmentation due to enzymatic deficiencies; 4, disease-related (post-inflammatory) hyperpigmentation. Freckles are areas where the melanocytes (pigment-making cells) are more active and responsive to UV radiation than in neighbouring skin. The increased pigmentation seen in pregnancy is due to the influence of estrogen, progesterone, and melanocyte-stimulating hormone. Hormonally related hyperpigmentation, such as that occurring in pregnancy, can also show up as a condition called the mask of pregnancy, or melasma. This is a condition in which blotches of pigmentation appear on the face or in sun-exposed areas. Melasma is harmless. The pigment seen in melasma mostly goes away within several months of delivery. Individuals with a deficiency in the liver enzyme that metabolizes carotenes may develop a yellow/orange skin colour upon consumption of large quantities of carrots, peppers, or other yellow/orange vegetables. Post-inflammatory hyperpigmentation (PIH) is a frequently encountered problem and represents the sequelae of various cutaneous disorders as well as therapeutic interventions. This acquired excess of pigment can be attributed to various preceding disease processes that affect the skin; these processes include infections, allergic reactions, mechanical injuries, reactions to medications, phototoxic eruptions, trauma (e.g., burns), and inflammatory diseases (e.g., lichen planus, lupus erythematosus, atopic dermatitis, psoriasis and sarcoidosis).

Postinflammatory Hyperpigmentation

PIH is caused by 1 of 2 mechanisms that result in either epidermal melanosis or dermal melanosis. The epidermal inflammatory response (i.e., dermatitis) results in the release and subsequent oxidation of arachidonic acid to prostaglandins, leukotrienes, and other products. These products of inflammation alter the activity of both immune cells and melanocytes. Specifically, these inflammatory products stimulate epidermal melanocytes, causing them to increase the synthesis of melanin and subsequently to increase the transfer of pigment to surrounding keratinocytes. Such increased stimulation and transfer of melanin granules results in epidermal hypermelanosis. On the contrary, dermal melanosis occurs when inflammation disrupts the basal cell layer, causing melanin pigment to be released and subsequently trapped by macrophages in the papillary dermis, also known as pigmentary incontinence.

PIH is a universal response of the skin, but it is more common in pigmented, darker skin. The distribution of the hypermelanotic lesions depends on the location of the original inflammatory dermatosis. The colour of the lesions ranges from light brown to black, with a lighter brown appearance if the pigment is within the epidermis (i.e., epidermal melanosis) and a darker grey appearance if lesions contain dermal melanin (i.e., dermal melanosis). PIH can occur with various disease processes that affect the skin. These processes include allergic reactions, infections, trauma, and phototoxic eruptions. Common inflammatory diseases that result in PIH include acne, lichen planus, systemic lupus erythematosus, chronic dermatitis, and cutaneous T-cell lymphoma, especially erythrodermic variants, psoriasis and sarcoidosis.

Treatment of Hyperpigmentation and Inflammatory Skin Conditions with Deoxynojirimycin Analogues.

The role of glycosphingolipids in inflammation has been extensively discussed in the previous section. Importantly, an absolute requirement for melanin production in melanocytes is the presence of glycosphingolipids like glucosylceramide. Glycolipid negative melanoma cell lines lacking glucosylceramide synthase activity differ from their parental cells with normal glycosphingolipid synthesis by the lack in melanin. Addition of glycosphingolipid or transfection with glucosylceramide synthase cDNA restores melanin production, indicating that synthesis of glucosylceramide (and/or other glycosphingolipids) is essential for melanin production in the melanosome. The production of glycosphingolipids such as glucosylceramide seems required for proper sorting of tyrosinase to the melanosomes.

It has now been found that overproduction of glycosphingolipids is a key factor in inflammatory processes in the skin and thus may intrinsically cause overproduction of melanin (hyperpigmentation). We postulate that overproduction of glycosphingolipids (as the result of local inflammatory conditions) causes increased local melanin synthesis (see scheme below). Inhibitors of glycosphingolipid synthesis, such as the deoxynojirimycin analogues, according to the present invention, can reduce the excessive melanin production and associated hyperpigmentation.

Hence, the deoxynojirimycin analogues, or pharmaceutically acceptable salts thereof, according to the present invention can suitably be used for the treatment of hyperpigmentation and inflammatory skin conditions. So far approaches to interfere in melanin production have aimed at other targets in the process of melanogenesis than glycosphingolipid synthesis. Many depigmentating agents act as alternative substrates of tyrosinase thus inhibiting the first enzymatic step in melanin synthesis the conversion of tyrosine to dopaquinone, leading to the melanin polymer. Although usually reduces or removes hyperpigmentations quite effectively, it may cause also cause ochronosis (black speckling in the dermis) in patients with darker skins. Moreover, hydroquinones have been banned in parts of Europe and all throughout Asia due to the belief that higher concentrations are carcinogenic.

Specific Deoxynojirimycin Analogues for the Treatment of Hyperpigmentation and Skin Inflammatory Processes Iminosugars were designed that harbour optimal features for use in skin. Ceramide and glucosylceramide are important structural components of the stratum corneum and regulate water permeability of the skin. It is known that glucosylceramides together with other polar lipids are secreted into the extracellular space of the stratum corneum by lamellar bodies and are subsequently processed to ceramides. The lysosomal glucocerebrosidase plays a role in this process as suggested by the fact that a complete deficiency in this enzyme is accompanied by markedly impaired epidermal barrier function. Iminosugars should therefore not interfere with the crucial generation of ceramide from glucosylceramide catalysed by lysosomal glucocerebrosidase. Given this prerequisite, the iminosugar ido-N-(5-adamantane-1-yl-methoxy-pentyl) deoxynojirimycin was found to be an ideal compound (Table 5). Ido-N-(5-adamantane-1-yl-methoxy-pentyl)deoxynojirimycin is able to inhibit glucosylceramide synthase activity and reduce melanin production in human melanocytes.

TABLE 5

IC50 values (uM) in melanoma cells

| Iminosugar | GC synthase | Non-lysosomal GCase | Lysosomal GCase |
|---|---|---|---|
| N-butyl-deoxynojirimycin | 35 | 0.5 | >100 |
| Nonyl-DNM | 0.8 | 0.003 | 2.0 |
| Ido-N-(5-adamantane-1-yl-methoxy-pentyl)deoxynojirimycin | 2.5 | 0.003 | >100 |

Various iminosugars were analysed with respect to ability to inhibit glucosylceramide synthase, non-lysosomal glucosylceramidase and lysosomal glucocerebrosidase in cultured melanoma cells. Inhibition of the two first enzyme activities is desired whilst inhibition of the latter activity is not. In vivo glucocerebrosidase activity, non-lysosomal glucosylceramidase activity and glucosylceramide synthase activity was determined according to the procedure described in J. Biol. Chem, 273,26522-27 (1998). Briefly, in vivo glucocerebrosidase and non-lysosomal glucosylceramidase activity was measured by exposing cells to fluorescent C6-NBD-glucosylceramide complexed to albumin. The conduritol-B-epoxide sensitive and insensitive degradation of C6-NBD-glucosylceramide to C6-NBD-ceramide was analysed following harvesting of cells, lipid extraction and quantitative thin layer chromatography. The activity that is inhibited by Conduritol-B-epoxide can be attributed to glucocerebrosidase and the remainder to the non-lysosomal glucosylceramidase. In vivo glucosylceramide synthase activity was measured by exposing cells to fluorescent C6-NBD-ceramide complexed to albumin. The conversion of C6-NBD-ceramide to C6-NBD-glucosylceramide was analysed following harvesting of cells, lipid extraction and quantitative thin layer chromatography.

Inhibition of glycosphingolipid synthesis with ido-N-(5-adamantane-1-yl-methoxy-pentyl)deoxynojirimycin in the MEB4 culture results in loss of pigmentation. Two melanoma cultures, one dark pigmented (An) and the other very lightly pigmented (M14) show a clearly higher content of glucosylceramide (GlcCer) in the darkly pigmented culture both in the total cell extract and in a melanosomal fraction.

In the melanocyte even within a single culture passage a significant decrease in pigmentation is found with cells of the lighter and darker skin type upon exposure to ido-N-(5-adamantane-1-yl-methoxy-pentyl)deoxynojirimycin. The pharmaceutical application of the deoxynojirimycin analogues according to the invention and will be in post-inflammatory hyperpigmentation and skin inflammatory conditions. There is strong evidence that when administered systemically these deoxynojirimycin analogues have strong anti-inflammatory activity in vivo. They shows attractive pharmacological features (good bioavailability, lack of metabolism, no adverse toxicological effects upon 2 weeks dosing in animals). Ido-N-(5-adamantane-1-yl-methoxy-pentyl)deoxynojirimycin is particularly suited for skin application since it does not/hardly inhibit lysosomal glucocerebrosidase, a key enzyme activity for skin integrity.

6. Melanoma and Other Tumors

Tumor cells contain gangliosides on their surface and actively shed them whereafter they are taken up by other cells. It has been reported that tumor gangliosides have immunosuppressive activity, proangiogenic properties and stimulate growth-factor mediated fibroblast and vascular endothelial cell proliferation. Increased expression of gangliosides has been associated with enhanced tumor formation and accelerated progression. Inhibition of ganglioside biosynthesis may impede tumor progression and/or decrease metastasis. An iminosugar inhibitor of glucosylceramide synthase (OGT2378) was shown to exert a marked inhibition of melanoma tumor growth in a mouse model.

Deoxynojirimycin Analogues for Treatment of Melanoma and Other Tumors

It has now been found that iminosugars that are potent and specific inhibitors of glucosylceramide synthase as well as non-lysosomal glucosylceramidase can reduce tumor growth and/or metastasis. Concomitant inhibition of both enzyme activities is required for an optimal efficacy.

The deoxynojirimycin analogues according to the present invention harbour all desired features including a good bioavailability, lack of metabolism and toxicity. Therefore, the deoxynojirimycin analogues, or pharmaceutically acceptable salts thereof, according to the present invention can suitable be used for the treatment of melanoma and other tumors.

Experimental Data

Various iminosugars were analysed with respect to ability to inhibit glucosylceramide synthase, non-lysosomal glucosylceramidase and lysosomal glucocerebrosidase in cultured melanoma cells. Inhibition of the two first enzyme activities is desired whilst inhibition of the latter activity is not.

TABLE 6

IC50 values (uM) in melanoma cells

| Iminosugar | GC synthase | Non-lysosomal GCase | Lysosomal GCase |
|---|---|---|---|
| N-butyl-deoxynojirimycin | 35 | 0.5 | >100 |
| Nonyl-DNM | 0.8 | 0.003 | 2.0 |
| Ido-N-(5-adamantane-1-yl-methoxy-pentyl)deoxynojirimycin | 2.5 | 0.003 | >100 |

In vivo glucocerebrosidase activity, non-lysosomal glucosylceramidase activity and glucosylceramide synthase activity was determined according to the procedure described in J. Biol. Chem, 273, 26522-27 (1998). Briefly, in vivo glucocerebrosidase and non-lysosomal glucosylceramidase activity was measured by exposing cells to fluorescent C6-NBD-glucosylceramide complexed to albumin. The conduritol-B-epoxide sensitive and insensitive degradation of C6-NBD-glucosylceramide to C6-NBD-ceramide was analysed following harvesting of cells, lipid extraction and quantitative thin layer chromatography. The activity that is inhibited by Conduritol-B-epoxide can be attributed to glucocerebrosidase and the remainder to the non-lysosomal glucosylceramidase. In vivo glucosylceramide synthase activity was measured by exposing cells to fluorescent C6-NBD-ceramide complexed to albumin. The conversion of C6-NBD-ceramide to C6-NBD-glucosylceramide was analysed following harvesting of cells, lipid extraction and quantitative thin layer chromatography.

Animal Model to Monitor Efficacy of Selected Deoxynojirimycin Analogues.

Ido-N-(5-adamantane-1-yl-methoxy-pentyl)deoxynojirimycin can be administered orally in the powdered chow. Use can be made of C57BL/6 mice injected intradermally with MEB4 cells, asubline of B16 murine melanoma cells (Riken Cell Bank, Saitama, Japan). Mice can be examined for tumor formation and size three times weekly. Tumor size can be measured in three dimensions using callipers and tumor volume can be estimated using the formula a×b×c/2 (Weiss et al. 2003. Cancer Research 63, 3654-8).

7. Fungal Diseases

It has been recently become apparent that pathogenic fungi possess an enzyme homologous to the human glucosylceramide synthase. Glucosylceramides are produced selectively during hyphal growth and are concentrated in the cell membrane adjacent to the growth tip. Inhibition of hyphal growth has been observed following exposure of fungi to an analogue of ceramide that is known to inhibit glucosylceramide synthase activity.

It has now been found that carefully selected hydrophobic iminosugars are more potent and well tolerated inhibitors of glucosylceramide synthase. Selection of an iminosugar that specifically interferes with fungal glucosylceramide synthase activity and only poorly affects the endogenous human glucosylceramide synthase can be employed to combat life-threatening fungal infections. Such infections constitute a growing problem in the clinic. Selected iminosugars could be used in combination with recombinant human chitotriosidase, a chitinase that attacks the cell wall at the growth tip of fungal hyphae. Accordingly, the deoxynojirimycin analogues, or pharmaceutically acceptable salts thereof, according to the present invention can suitably be used for the treatment of fungal diseases.

8. Viral Infections

Iminosugars have been investigated as agents for the treatment of viral infections. Studies with N-butyldeoxynojirimycin to treat infection with HIV, the causative agent of AIDS, have been conducted. AIDS affects several hundred million individuals worldwide. Viral infectivity and syncytium formation was noted in vitro. Phase II clinical trials with N-butyldeoxynojirimycin as anti-HIV agent did not render encouraging result. At required serum concentrations major side effects occurred. Hepatitis B virus (HBC) infects over 350 million people worldwide and can cause liver disease and hepatocellular carcinoma. In woodchucks chronically infected with woodchuck hepatitis virus, a closely related animal model of HBV infection, treatment with nonyldeoxynojirimycin was found to prevent the secretion of infectious enveloped virus. Worldwide, more than 100 million people are chronically infected with the hepatitis C virus (HCV). In the absence of a vaccine this represents one of the most serious threats to the public health of developed nations. With an estimated 3.9 million North Americans chronically infected, hepatitis C is now the leading reason for liver transplantation in the United States. It causes about 8,000 U.S. deaths annually, a number that is expected to triple in the next 20 years in the absence of effective intervention.

The iminosugar N-nonyldeoxynojirimycin has shown antiviral activity in bovine viral diarrhoea virus, an in vitro surrogate model of hepatitis C.

It is believed that ER α-glucosidases are responsible for the stepwise removal of terminal glucose residues from N-glycan chains attached to nascent glycoproteins. This enables the glycoproteins to interact with the ER chaperones calnexin and calreticulin, which bind exclusively to monoglucosylated glycoproteins. Interaction with calnexin is crucial for the correct folding of some but not all glycoproteins, and inhibitors of the glucosidases can be used to specifically target proteins that depend on it. The antiviral activity of deoxynojirimycins is thought to be based on inhibition of ER α-glucosidases would lead to disruption of the proper folding and transport of viral envelope glycoproteins and prevent the secretion of infectious enveloped virus.

We postulate, however, that the observed antiviral activity of iminosugars is not based on inhibition of ER a-glucosidases but rather on inhibition of synthesis of glucosylceramide and its glycosphingolipid metabolites. Glycosphingolipid-rich rafts on the surface of the host cell are likely to be of key importance in fusion and budding of viruses. Manipulation of surface glycosphingolipid composition will affect these processes.

This novel insight renders a new rationale for selection of iminosugars for the treatment of viral infections. Compounds have to be selected primarily on the criterion that they are potent inhibitors of glucosylceramide synthase activity. Furthermore, the compounds should be well bioavailable and well tolerated. The deoxynojirimycin analogues according to the present invention, in particular ido-N-(5-adamantane-1-yl-methoxy-pentyl)deoxynojirimycin. Hence, the deoxynojirimycin analogues, or pharmaceutically acceptable salts thereof, according to the present invention can suitably be used for the treatment of viral fulfil these criteria.

9. Microbial Infections and Endotoxins Mucosal Infections

Mucosal pathogens target sites of infection through specific adherence to host glycoconjugate receptors. As a consequence, depletion of such receptors from the cell surface may be expected to inhibit attachment, impair bacterial colonization and reduce the activation of mucosal inflammation. Inhibitors of glycosphingolipid synthesis can be used to deplete receptors.

N-butyl-deoxynojirimycin treated mice indeed reduced susceptibility to experimental urinary tract infection with P-fimbriated *E. coli* (Svensson et al. Mol. Microbiol. 2003; 47:453-61). The mucosal inflammatory response was impaired, as shown by reduced chemokine secretion and lower neutrophil recruitment, and the bacteria colonized the urinary tract less efficiently than in normal mice. *E. coli* species which cause urinary tract infections (UTI) typically have fimbriae with a terminal receptor for the "P" antigen. The P antigen is a blood group marker which is also found on the surface of cells lining the perineum and urinary tract. Approximately 75% of the population expresses the P antigen, and these individuals are particularly susceptible to UTI's. The P antigen is also found in vaginal and prostatic secretions: these secreted P antigens are protective in that they bind to the bacterial receptor, preventing binding of the organism to the surface epithelium. The individuals most susceptible to UTI are those who express P antigen on their cells and lack P antigen in their secretions.

Another example forms *Helicobacter pylori* that causes complex disseminated gastric inflammation. It has therefore now been found that glycosphingolipids are also crucial for its firm adhesion to the mucosa. Depletion of gastric glycosphingolipids by appropriate iminosugars could have great therapeutic use.

Endotoxins

It has further been found that Glycolipid receptors can not only act as the primary interface between bacteria and their host, but also serve as target for bacterial virulence factors such as endotoxins. The ganglioside GM1 can act as a receptor for the B subunits of various AB5 toxins like Cholera toxin (CTX) or the heat-stable toxin II from *Escherichia coli* whereas the globotriaoside Gb3 is a receptor for the AB5-toxin Shiga toxin (ST) and some related toxins like Verotoxin. Prevention of endotoxin binding is of great clinical relevance. For example, verotoxins are involved in endothelial targeting in the microangiopathies of hemorrhagic colitis and hemolytic uremic syndrome (HUS). Inhibitors of glycosphingolipid synthesis could be employed to intervene in endotoxin-mediated pathology.

Deoxynojirimycin Analogues for the Treatment of Mucosal Bacterial Infections and Prevention of Endotoxin-Mediated Pathology The above novel insights renders a rationale for selection of iminosugars for the treatment of viral infections. Compounds have to be selected primarily on the criterion that they are potent inhibitors of glucosylceramide synthase activity. Furthermore, the compounds should be well bioavailable and well tolerated. The present deoxynojirimycin analogues, in particular Ido-N-(5-adamantane-1-yl-methoxy-pentyl)deoxynojirimycin fulfil these criteria. Hence, the deoxynojirimycin analogues, or pharmaceutically acceptable salts thereof, according to the present invention can suitably be used for the treatment of mucosal bacterial infections ans prevention of endotoxin-mediated pathology.

BREIF DESCRIPTION OF THE DRAWINGS

FIG. 1. Design of suitable hydrophobic entities
FIG. 2. Synthesis of deoxynojirimycin analogue 4.
FIG. 3. Synthesis of deoxynojirimycin 7.
FIG. 4. Synthesis of deoxynojirimycin analogues 17, 18 and 19.

Figure 5:
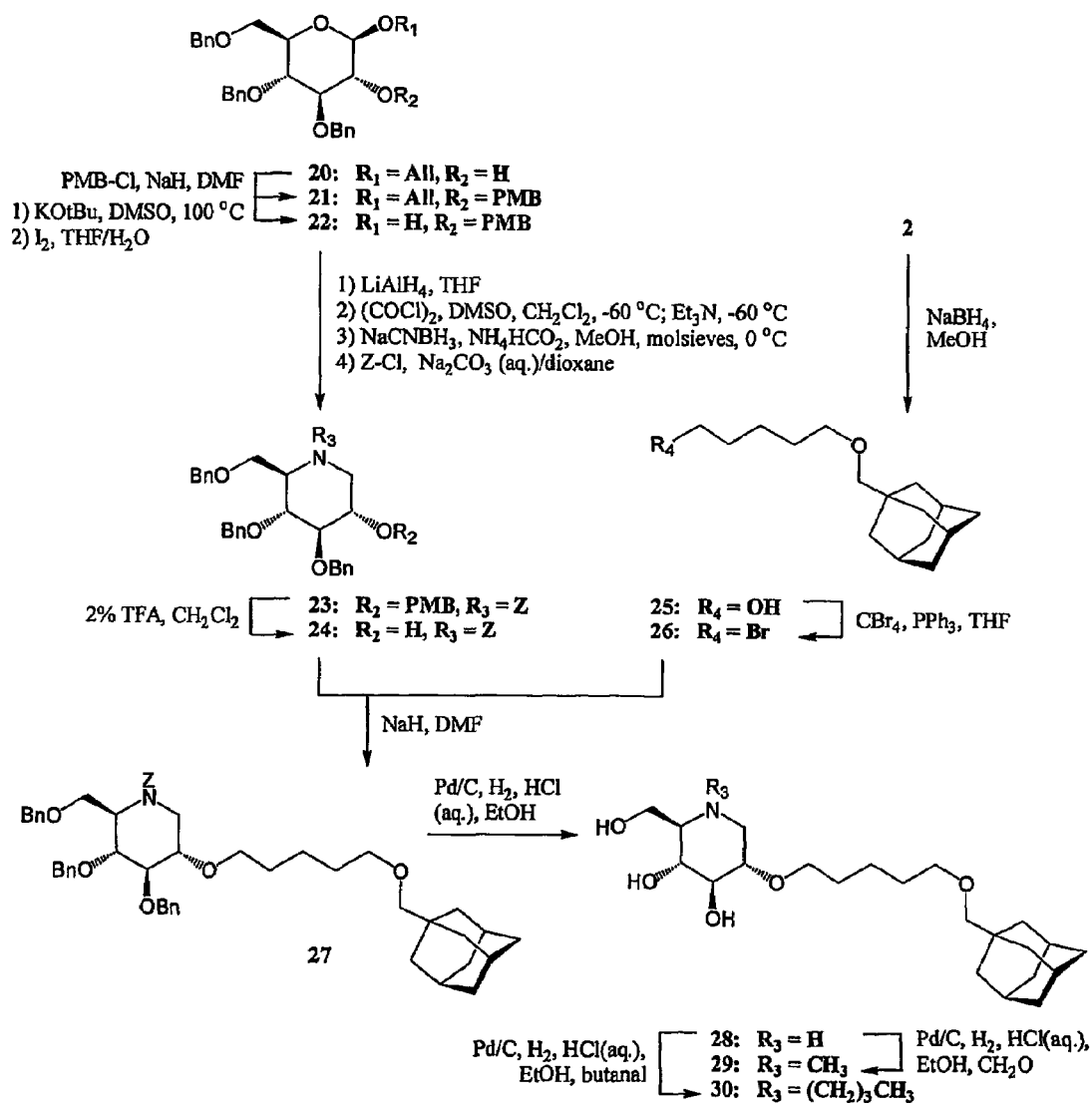

FIG. 5. Synthesis of deoxynojirimycin analogues 28, 29 and 30.

REFERENCES

1. Kolter T, Proia R L and Sandhoff K. 2002. J. Biol. Chem. 277, 25859-62. Combinatorial ganglioside biosynthesis.
2. Wertz P W & van den Bergh B. 1998. Chem. Phys. Lipids 91, 85-96. The physical, chemical and functional properties of lipids in the skin and other biological barriers.
3. Simons K & van Meer G. 1988. Biochemistry 27, 6197-6202. Lipid sorting in epithelial cells.
4. Brown D A & London E. 1998. J. Membr. Biol. 164, 103-114. Structure and origin of ordered lipid domains in biological membranes.
5. Hakomori S. 1981. A. Rev. Biochem. 50, 733-764. Glycosphingolipids in cellular interaction.
6. Huwiler A, Kolter T, Pfeilschifter J & Sandhoff K 2000. Biochim. Biophys. Acta 1485, 63-99. Physiology and pathophysiology of sphingolipid metabolism and signaling.
7. Hannun Y A & Obeid L M. 1995. Trends Biochem. Sci. 20, 73-77. Ceramide: an intracellular signal for apoptosis.
8. Kolesnick R & Kronke M. 1988. Annu. Rev. Physiol. 60, 643-665. Regulation of ceramide production and apoptosis.
9. van Blitterswijk W J, van der Luit A H, Veldman R J, Verheij M, & Borst J. 2003. Biochem J. 2003 January 15;369(Pt 2):199-211. Ceramide: second messenger or modulator of membrane structure and dynamics?
10. Merrill A H. 2002. J. Biol. Chem. 277, 25843-25846. De novo sphingolipid biosynthesis: a necessary, but dangerous, pathway.
11. Sandhoff K & Kolter T. 2003. Philos Trans R Soc Lond B Biol Sci. 358(1433):847-61. Biosynthesis and degradation of mammalian glycosphingolipids.
12. Van Weely S, Brandsma M, Strijland A, Tager J M & Aerts J M F G. 1993. Biochim. Biophys. Acta 1181,55-62. The existence of a non-lysosomal glucocerebrosidase that is not deficient in Gaucher disease.
13. Aerts J M, Hollak C, Boot R, & Groener A. 2003. Philos Trans R Soc Lond B Biol Sci. 358(1433):905-14. Biochemistry of glycosphingolipid storage disorders: implications for therapeutic intervention.
14. Barranger J A & Ginns E I. 1989. Glycosylceramide lipidosis: Gaucher disease. In: Scriver C R, Beaudet A L, Sly W S, Vall D (eds) The metabolic basis of inherited disease. McGraw-Hill, New York, p 1677-1698
15. Beutler E & Grabowski G A. 1995. Gaucher's disease. In: Scriver C R, Beaudet A L, Sly W S, Valle D (eds) The metabolic and molecular bases of inherited disease. McGraw-Hill, New York, p 2641-2670
16. Brady R O, Kanfer J N, Bradley R M & Shapiro D. 1966. Demonstration of a deficiency of glucocerebroside-cleaving enzyme in Gaucher's disease. J Clin Invest 45, 1112-1115
17. Patrick A D. 1965. A deficiency of glucocerebrosidase in Gaucher's disease. Biochem J 97, 17c-18c
18. Van Weely S, van den Berg M, Barranger J A, Sa Miranda M C, Tager J M & Aerts J M F G. 1993. Role of pH in determining the cell-type specific residual activity of glucocerebrosidase in type 1 Gaucher disease. J Clin Invest 91, 1167-1175
19. Aerts J M, van Weely S, Boot R, Hollak C E & Tager J M. 1993. Pathogenesis of lysosomal storage disorders as illustrated by Gaucher disease. J Inherit Met Dis 16, 288-291

20. Cox T M, & Schofield J P. 1997. Gaucher's disease: clinical features and natural history Baillieres Clin. Hematol. 10, 657-689
21. Aerts J M F G & Hollak C E M. 1997. Plasma and metabolic abnormalities in Gaucher's disease. Baillieres Clin Haematol 10, 691-709
22. Cox T M. 2001. Gaucher disease: understanding the molecular pathogenesis of sphingolipidoses. J Inherit Met Dis 24 (suppl 2), 106-121
23. Moran M T, Schofield J P, Hayman A R, Shi G-P, Young E & Cox T M. 2000. Pathologic gene expression in Gaucher disease: upregulation of cysteine proteinases including osteoclastic cathepsin K. Blood 96, 1969-1978
24. Brady R O. 1997. Gaucher's disease: past, present and future. Baillieres Clin Haematol 10, 621-634
25. Barranger J A, & O'Rourke E. 2001. Lessons learned from the development of enzyme therapy for Gaucher disease J Inherit Met Dis 24 (suppl 2), 89-96
26. Hollak C E M, Aerts J M F G, Goudsmit E R, Phoa S S, Ek M. van Weely S, von dem Borne A E & van Oers M H. 1995. Individualised low-dose alglucerase therapy for type 1 Gaucher's disease. Lancet 345, 1474-1478
27. Richter J & Karlsson S. 2001. Clinical gene therapy in hematology: past and future. Int. J Hematol 73, 162-169
28. Radin N S. 1996. Treatment of Gaucher disease with an enzyme inhibitor. Glycoconj J 13, 153-157
29. Platt F M, Jeyakumar M, Andersson U, Priestman D A, Dwek R A, Butters T D, Cox T M, Lachmann R H, Hollak C E M, Aerts J M F G, Hrebicek M, Moyses C, Gow I, Elstein D & Zimran A. 2001. J. Inher. Met. Dis. 24, 275-290. Inhibition of substrate synthesis as a strategy for glycolipid lysosomal storage disease therapy.
30. Lee L, Abe A & Shayman J A. 1999. J Biol Chem 274, 146662-14665 Improved inhibitors of glucosylceramide synthase.
31. Abe A, Gregory S, Lee L, Killen P D, Brady R O, Kulkarni A & Shayman J A. 2000. Reduction of globotriaosylceramide in Fabry disease mice by substrate deprivation. J Clin Invest 105, 1563-1567
32. Platt F M, Neises G R, Dwek R A & Butters T D. 1994. N-butyl-deoxynojirimycin is a novel inhibitor of glycolipid biosynthesis. J Biol Chem 269, 8362-8365
33. Jeyakumar M, Butters T D, Cortina-Borja M, Hunnam V, Proia R L, Perry V H, Dwek R A & Platt F M. 1999. Delayed symptom onset and increased life expectancy in Sandhoff mice treated with N-butyl-deoxynojirimycin. Proc Natl Acad Sci USA 96, 6388-6393
34. Andersson U, Butters T D, Dwek R A & Platt F M. 2000. N-butyldeoxygalactonojirimycin: a more selective inhibitor of glycosphingolipid biosynthesis than N-butyldeoxynojirimycin, in vitro and in vivo. Biochem Pharmacol 49, 821-829
35. Overkleeft H S, Renkema G H, Neele J, Vianello P, Hung I O, Strijland A, van den Burg A, Koomen, G J, Pandit U K & Aerts J. 1998. Generation of specific deoxynijirimycin-type inhibitors of the non-lysosomal glucosylceramidase. J Biol Chem 273, 26522-26527
36. Cox T, Lachmann R, Hollak C, Aerts J, van Weely S, Hrebicek M, Platt F, Butters T, Dwek R, Moyses C, Gow I, Elstein D & Zimran A. 2000. Lancet. 355(9214):1481-5. Novel oral treatment of Gaucher's disease with N-butyldeoxynojirimycin (OGT 918) to decrease substrate biosynthesis.
37. Heitner R, Elstein D, Aerts J, Weely S & Zimran A. 2002. Low-Dose N-Butyldeoxynojirimycin (OGT 918) for Type I Gaucher Disease. Blood Cells Mol Dis 28, 127-33
38. Fischl M A, Resnick L, Coombs R, Kremer A B, Pottage J C Jr, Fass R J, Fife K H, Powderly W G, Collier A C, Aspinall R L, et al. The safety and efficacy of combination N-butyl-deoxynojirimycin (SC-48334) and zidovudine in patients with HIV-1 infection and 200-500 CD4 cells/mm3. J Acquir Immune Defic Syndr. 1994 February;7(2): 139-47.
39. Goss P E, Reid C L, Bailey D & Dennis J W. 1997. Phase 1B clinical trial of the oligosaccharide processing inhibitor swainsonine in patients with advanced malignancies.

The invention claimed is:

1. Deoxynojirimycin analogue, or a pharmaceutically acceptable salt thereof, having the general structure (I)

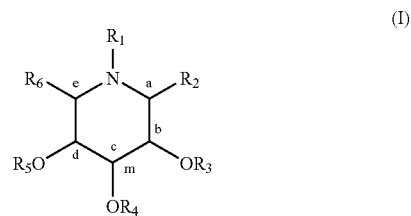

wherein $R_1$-$R_5$ each independently comprise H or $(CH_2)_n CH_3$ or X; n is 0-9
$R_6$ comprises H, $CH_2OH$ or $CH_2OX$;
m is 0 or 1;
a, b, c, d, e are chiral centers having an R or S configuration;
and X comprises a large hydrophobic moiety and a spacer, whereby the hydrophobic moiety is linked through the spacer to the nitrogen atom or carbon atom concerned, and wherein the large hydrophobic moiety is derived from a polycyclic alcohol containing three or more rings each sharing two or more carbon atoms with one of the other rings and is capable of inserting in lipid bilayers.

2. Deoxynojirimycin analogue, or a pharmaceutically acceptable salt thereof, according to claim 1, wherein the large hydrophobic moiety is linked to said nitrogen atom of the deoxynojirimycin by means of a spacer comprising an alkoxy polyalkylene or polyalkylene chain of from 3 to 8 carbon atoms.

3. Deoxynojirimycin analogue, or a pharmaceutically acceptable salt thereof, according to claim 1, wherein the large hydrophobic moiety is derived from a compound selected from the group consisting of adamantanemethanol, cholesterol, β-cholestanol, adamantanol and 9-hydroxyphenanthrene.

4. Deoxynojirimycin analogue, or a pharmaceutically acceptable salt thereof, according to claim 1, having the ido-configuration.

5. Deoxynojirimycin analogue comprising ido-N-(5-adamantane-1-yl-methoxy pentyl)deoxynojirimycin, or a pharmaceutically acceptable salt thereof.

6. A method of treating a disease or condition involving increased levels of glucosylceramide and glucosphingolipids comprising administering an effective amount of a Deoxynojirimycin analogue according to claim 1 to a person in need thereof.

7. A method of treating a disease or condition involving increased levels of glucosylceramide glucosphingolipids and glucosidases comprising administering an effective amount of a Deoxynojirimycin analogue according to claim 1 to a person in need thereof.

8. The method of claim 6 wherein the disease is Gaucher disease.

9. The method of claim 6 wherein the disease is an inflammatory disease.

10. The method of claim 6 wherein the condition is hyperpigmentation and/or an inflammatory skin condition.

11. The method of claim 6 wherein the disease is a fungal disease.

12. The method of claim 6 wherein the condition is overweight or obesity.

13. The method of claim 6 wherein the disease is a lysosomal storage disorders.

14. The method of claim 6 wherein the condition is melanoma or a tumor.

15. The method of claim 6 wherein the disease is a microbacterial infection.

16. The method of claim 7 wherein the condition is insulin resistance.

17. Pharmaceutical composition comprising a deoxynojirimycin analogue, or pharmaceutically acceptable salt thereof, according to claim 1 and a pharmaceutically acceptable carrier.

18. Method of treatment of an individual suffering from a disease selected from the group consisting of insulin resistance Gaucher disease, inflammatory diseases, hyperpigmentation and/or inflammatory skin conditions, overweight and obesity, lysosomal storage disorders, fungal diseases, melanoma and other tumors, and microbacterial infections, comprising administrating to said individual an effective amount of the pharmaceutical composition according to claim 17.

* * * * *